United States Patent [19]

Miller

[11] Patent Number: 5,225,418

[45] Date of Patent: Jul. 6, 1993

[54] 5H-(1,2)BENZISOTHIAZOLO(2,3-A)QUINO-LINE-5-ONES AND ANALOGS AS ANTIINFLAMMATORY AGENTS

[75] Inventor: William H. Miller, Glen Mills

[73] Assignee: Du Pont Merck Pharmaceutical Company, Wilmington, Del.

[21] Appl. No.: 808,712

[22] Filed: Dec. 17, 1991

[51] Int. Cl.$^5$ ............... C07D 498/04; C07D 497/04; A61K 31/44; A61K 31/38
[52] U.S. Cl. ................................. 514/285; 546/62
[58] Field of Search ..................... 546/62; 514/285

[56] References Cited

U.S. PATENT DOCUMENTS 4,397,858 8/1983 Welter et al. ............... 548/209
4,550,168 10/1985 Welter et al. ............... 546/270

Primary Examiner—C. Warren Ivy
Assistant Examiner—Phyllis G. Spivack
Attorney, Agent, or Firm—Blair Q. Ferguson

[57] ABSTRACT

The present invention relates to novel 5H-[1,2]benzisothiazolo[2,3-a]quinoline-5-ones, processes for preparing such compounds, to pharmaceutical compositions containing such compounds, and to methods of using these compounds for the treatment of inflammatory disorders.

16 Claims, No Drawings

5H-(1,2)BENZISOTHIAZOLO(2,3-A)QUINOLINE-5-ONES AND ANALOGS AS ANTIINFLAMMATORY AGENTS

FIELD OF THE INVENTION

The present invention relates to novel 5H-[1,2]benzisothiazolo[2,3-a]quinoline-5-ones, processes for preparing such compounds, to pharmaceutical compositions containing such compounds, and to methods of using these compounds for the treatment of inflammatory disorders.

BACKGROUND OF THE INVENTION

Inflammatory diseases are a widespread cause of human suffering and loss of function. Additionally, the treatment of patients with these diseases represents a very large expense in terms of money, facilities and personnel. The incidence of many such diseases is expected to rise in the future as life expectancy and the median age of the population continue to increase.

Inflammatory diseases are known which affect many diverse tissues and organs in the body. Examples of diseases in which the inflammation is most apparent in the joints and related connective tissue are osteoarthritis, rheumatoid arthritis, tendonitis, bursitis, and the like. These diseases are most often treated with nonsteroidal antiinflammatory agents such as aspirin, ibuprofen, and piroxicam, or with antiinflammatory glucocorticosteroids. However, these treatments suffer either from a lack of efficacy in completely controlling the disease process, or from unacceptable toxic side effects.

Arthritis is a progressive disorder of unknown cause that principally affects the hands and large weight-bearing joints and is clinically characterized by pain, deformity, and limitation of motion. Pathologically, it is characterized by erosive lesions, cartilage destruction, subchondral sclerosis, cyst formation, and osteophytes at the joint margins. Arthritis is a potentially crippling disease that is second only to cardiovascular diseases in producing severe chronic disability (Epstein, New England J. Med. (1989) 239: 1322). It affects nearly 10 percent of the population over age 60. This high incidence rate results in billions of dollars in costs annually for medications, surgery, and lost productivity (Peyron, Clin. Orthop. (1986) 213: 13; Holbrook, Am. Acad. Orthopaedic Surgeons (1984) 1). Thus a treatment to arrest and/or reverse the progress of arthritis would be of considerable benefit to mankind.

The compounds of the present invention, 5H-[1,2]benzisothiazolo[2,3-a]quinoline-5-ones, represent a novel structural class, and no previous investigations into their preparation or antiinflammatory properties have been reported.

Welter et al., U.S. Pat. No. 4,352,799 discloses 2-phenyl-1,2-benzisoselenazol-3(2H)-one (ebselen) as an antiinflammatory agent.

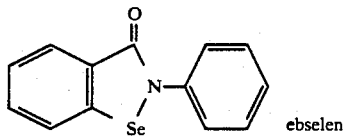
ebselen

Welter et al., U.S. Pat. No. 4,550,168 discloses related 2-phenyl-1,2-benzisoselenazol-3(2H)-ones

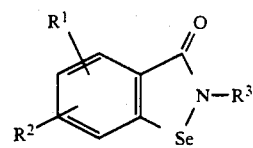

as being useful for the treatment of inflammatory diseases.

Welter et al., U.S. Pat. No. 4,397,858 discloses a series of 2-halogenophenyl-1,2-benzisothiazol-3(2H)-ones

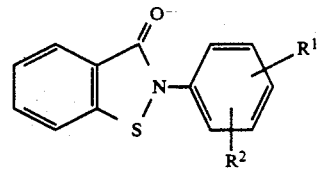

wherein $R^1$ represents F, Cl, or Br, and $R^2$ represents H, F, Cl, or Br, and claim them to be useful in the treatment of phlogistic and/or arteriosclerotic processes.

None of the references cited above disclose the compounds of the present invention or suggest that such compounds would possess activity as antiinflammatory agents or that they might be of value in the treatment of arthritis.

DETAILED DESCRIPTION OF THE INVENTION

The present invention provides compounds of the Formula

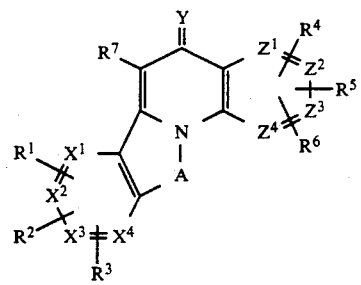

or a pharmaceutically acceptable salt or prodrug form thereof, wherein:

$X^1$, $X^2$, $X^3$, and $X^4$ are independently CH or N, provided that 0–3 of X are N with the remaining X groups being CH;

$Z^1$, $Z^2$, $Z^3$, and $Z^4$ are independently CH or N, provided that 0–3 of Z are N with the remaining Z groups being CH;

Y is O or S;

A is S or Se;

$R^1$, $R^3$, $R^4$, $R^5$, and $R^6$ are independently selected from the following groups:
hydrogen;
$C_1$–$C_8$ alkyl substituted with 0–3 $R^{20}$;
$C_2$–$C_8$ alkenyl substituted with 0–3 $R^{20}$;
$C_2$–$C_8$ alkynyl substituted with 0–3 $R^{20}$;
$C_3$–$C_8$ cycloalkyl substituted with 0–3 $R^{20}$;
$C_6$–$C_{10}$ bicycloalkyl substituted with 0–3 $R^{20}$;
aryl substituted with 0–3 $R^{21}$; a $C_6$–$C_{14}$ carbocyclic residue substituted with 0–3 $R^{21}$;

a heterocyclic ring system substituted with 0-2 $R^{21}$, composed of 5-10 atoms including at least one nitrogen oxygen or sulfur atom;

F; Cl; Br; I; $NO_2$;

$OR^{12}$; $OC(=O)R^{12}$; $OC(=O)OR^{12}$; $OC(=O)ON(R^{12})_2$;

$N(R^{12})_2$; $NR^{12}C(=O)R^{12}$; $NR^{12}C(=O)OR^{12}$; $NR^{12}SO_2R^{12}$; $NR^{12}C(=O)N(R^{12})_2$;

$SO_3H$; $SR^{12}$; $S(O)R^{12}$; $SO_2R^{12}$; $SO_2N(R^{12})_2$;

$C(=O)R^{12}$; $CO_2R^{12}$; $C(=O)N(R^{12})_2$; $CSN(R^{12})_2$; $C(=O)NR^{12}OR^{12}$; and CN;

$R^1$ and $R^2$, when on adjacent carbon atoms, may alternatively be taken together to form $-OCH_2O-$ or $-OCH_2CH_2O-$;

$R^7$ is selected from the group consisting of:
hydrogen;
$C_1-C_8$ alkyl substituted with 0-3 $R^{20}$;
$C_2-C_8$ alkenyl substituted with 0-3 $R^{20}$;
$C_2-C_8$ alkynyl substituted with 0-3 $R^{20}$;
$C_3-C_8$ cycloalkyl substituted with 0-3 $R^{20}$;
$C_6-C_{10}$ bicycloalkyl substituted with 0-3 $R^{20}$;
aryl substituted with 0-3 $R^{21}$; a $C_6-C_{14}$ carbocyclic residue substituted with 0-3 $R^{21}$;
a heterocyclic ring system substituted with 0-2 $R^{21}$, composed of 5-10 atoms including at least one nitrogen, oxygen or sulfur atom;

F; Cl; Br; I; $NO_2$;

$OR^{12}$; $OC(=O)R^{12}$; $OC(=O)OR^{12}$; $OC(=O)ON(R^{12})_2$;

$N(R^{12})_2$; $NR^{12}C(=O)R^{12}$; $NR^{12}C(=O)OR^{12}$; $NR^{12}SO_2R^{12}$; $NR^{12}C(=O)N(R^{12})_2$;

$SO_3H$; $SR^{12}$; $S(O)R^{12}$; $SO_2R^{12}$; $SO_2N(R^{12})_2$;

$C(=O)R^{12}$; $CO_2R^{12}$; $C(=O)N(R^{12})_2$; $CSN(R^{12})_2$; $C(=O)NR^{12}OR^{12}$; and CN;

$R^{12}$ is independently selected at each occurence from the group consisting of:
hydrogen;
$C_1-C_8$ alkyl substituted with 0-3 $R^{20}$;
$C_2-C_8$ alkenyl substituted with 0-3 $R^{20}$;
$C_2-C_8$ alkynyl substituted with 0-3 $R^{20}$;
$C_3-C_8$ cycloalkyl substituted with 0-3 $R^{20}$;
$C_6-C_{10}$ bicycloalkyl substituted with 0-3 $R^{20}$;
aryl substituted with 0-3 $R^{21}$; a $C_6-C_{14}$ carbocyclic residue substituted with 0-3 $R^{21}$;
a heterocyclic ring system substituted with 0-2 $R^{21}$, composed of 5-10 atoms including at least one nitrogen, oxygen or sulfur atom;

$R^{20}$ is independently selected at each occurence from the group consisting of:
$C_1-C_5$ alkyl; $C_2-C_4$ alkenyl; $C_3-C_{10}$ cycloalkyl; $C_3-C_6$ cycloalkylmethyl; $C_2-C_6$ alkoxyalkyl;
$-C(=O)NR^{23}R^{24}$; $-C(=O)NR^{23}OR^{23}$; CN;
$-C(=NH)NHR^{23}$; $-CO_2R^{23}$; $-C(=O)R^{23}$;
$-CSN(R^{23})_2$;
$-OC(=O)R^{23}$; $-OC(=O)OR^{23}$; $-OR^{23}$; $-OC(=O)NR^{23}R^{24}$; $-NR^{23}R^{24}$;
$-NHC(=NH)NHR^{23}$; $-NR^{24}C(=O)R^{23}$;
$=NOR^{24}$; $-NR^{24}C(=O)OR^{24}$; $-NR^{23}C(=O)NR^{23}R^{24}$; $-NR^{24}SO_2NR^{23}R^{24}$; $-NR^{24}SO_2R^{23}$;
$SO_3H$; $SR^{23}$; $-S(=O)R^{23}$; $-SO_2R^{23}$;
$-SO_2NR^{23}R^{24}$ keto; F; Cl; Br; I; $NO_2$;
a $C_5-C_{14}$ carbocyclic residue substituted with 0-3 $R^{23}$;
aryl substituted with 0-3 $R^{21}$; or
a heterocyclic ring system substituted with 0-2 $R^{21}$, composed of 5 to 10 atoms including at least one nitrogen, oxygen or sulfur atom;

$R^{21}$, when a substituent on carbon, is independently selected at each occurence from the group consisting of:
phenyl, benzyl, phenethyl, phenoxy, benzyloxy, halogen, hydroxy, nitro, cyano, $C_1-C_5$ alkyl, $C_3-C_{10}$ cycloalkyl, $C_3-C_6$ cycloalkylmethyl, $C_7-C_{10}$ arylalkyl, $C_1-C_4$ alkoxy, $-NR^{23}R^{24}$, $C_2-C_6$ alkoxyalkyl, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1-C_4$ alkylcarbonyloxy, $C_1-C_4$ alkylcarbonyl, $C_1-C_4$ alkylcarbonylamino, $-SO_2R^{23}$, $-S(=O)R^{23}$, $-SO_2NR^{23}R^{24}$, $SO_3H$, $CF_3$, $OR^{23}$, CHO, $CH_2OR^{23}$, $CO_2R^{23}$, $C(=O)R^{23}$, $-NHSO_2R^{24}$, $-OCH_2CO_2H$, 2-(1-morpholino)ethoxy; or
a 5- or 6-membered heterocyclic ring containing from 1 to 4 heteroatoms selected from oxygen, nitrogen or sulfur;
or $R^{21}$ may be a 3- or 4- carbon chain attached to adjacent carbons on the ring to form a fused 5- or 6-membered ring, said 5- or 6- membered ring being optionally substituted on the aliphatic carbons with halogen, $C_1-C_4$ alkyl, $C_1-C_4$ alkoxy, hydroxy, or $-NR^{23}R^{24}$; or, when $R^{21}$ is attached to a saturated carbon atom, it may be carbonyl or thiocarbonyl;

$R^{21}$, when a substituent on nitrogen, is selected from one or more of the following:
phenyl, benzyl, phenethyl, hydroxy, $C_1-C_4$ hydroxyalkyl, $C_1-C_4$ alkoxy, $C_1-C_4$ alkyl, $C_3-C_6$ cycloalkyl, $C_3-C_6$ cycloalkylmethyl, $-NR^{23}R^{24}$, $C_2-C_6$ alkoxyalkyl, $C_1-C_4$ haloalkyl, $C_1-C_4$ alkoxycarbonyl, $C_1-C_4$ alkylcarbonyloxy, $C_1-C_4$ alkylcarbonyl;

$R^{23}$ is H, phenyl, benzyl or $C_1-C_6$ alkyl;
$R^{24}$ is H, phenyl, benzyl or $C_1-C_6$ alkyl;
$R^{23}$ and $R^{24}$ can alternatively join to form $-(CH_2)_4-$, $-(CH_2)_5-$, $-CH_2CH_2N(R^{25})CH_2CH_2-$, or $-CH_2CH_2OCH_2CH_2-$;
$R^{25}$ is H or $CH_3$.

Preferred compounds are those compounds of Formula I as described above, wherein:
$X^1$, $X^2$, $X^3$, and $X^4$ are independently CH or N, provided that 0-1 of X are N with the remaining X groups being CH;
$Z^1$, $Z^2$, $Z^3$, and $Z^4$ are independently CH or N, provided that 0-1 of Z are N with the remaining Z groups being CH;
Y is oxygen.
A is sulfur.
$R^1$, $R^2$, $R^3$, $R^4$, $R^5$, and $R^6$ are independently selected from the following groups:
hydrogen;
$C_1-C_8$ alkyl substituted with 0-1 $R^{20}$;
$C_2-C_8$ alkenyl substituted with 0-1 $R^{20}$;
$C_2-C_8$ alkynyl substituted with 0-1 $R^{20}$;
$C_3-C_8$ cycloalkyl substituted with 0-1 $R^{20}$;
$C_6-C_{10}$ bicycloalkyl substituted with 0-1 $R^{20}$;
aryl substituted with 0-3 $R^{21}$;
a heterocyclic ring system substituted with 0-2 $R^{21}$, composed of 5-10 atoms including at least one nitrogen, oxygen or sulfur atom;

F; Cl; Br; I; $NO_2$;
$OR^{12}$;
$N(R^{12})_2$; $NR^{12}C(=O)R^{12}$; $NR^{12}C(=O)OR^{12}$; $NR^{12}SO_2R^{12}$; $NR^{12}C(=O)N(R^{12})_2$;
$S(O)R^{12}$; $SO_2R^{12}$; $SO_2N(R^{12})_2$;

$C(=O)R^{12}$; $CO_2R^{12}$; $C(=O)N(R^{12})_2$; $C(=O)NR^{12}OR^{12}$; and CN;

$R^1$ and $R^2$, when on adjacent carbon atoms, may alternatively be taken together to form —OCH$_2$— or —OCH$_2$CH$_2$O—;

$R^7$ is selected from the group consisting of:
hydrogen;
$C_1$–$C_8$ alkyl substituted with 0–1 $R^{20}$;
$C_2$–$C_8$ alkenyl substituted with 0–1 $R^{20}$;
$C_2$–$C_8$ alkynyl substituted with 0–1 $R_{20}$;
$C_3$–$C_8$ cycloalkyl substituted with 0–1 $R^{20}$;
$C_6$–$C_{10}$ bicycloalkyl substituted with 0–1 $R^{20}$;
aryl substituted with 0–3 $R^{21}$;
a heterocyclic ring system substituted with 0–2 $R^{21}$, composed of 5–10 atoms including at least one nitrogen, oxygen or sulfur atom;
F; Cl; Br; I; NO$_2$;
OR$^{12}$;
N(R$^{12}$)$_2$; NR$^{12}$C(=O)R$^{12}$; NR$^{12}$C(=O)OR$^{12}$; NR$^{12}$SO$_2$R$^{12}$; NR$^{12}$C(=O)N(R$^{12}$)$_2$;
S(O)R$^{12}$; SO$_2$R$^{12}$; SO$_2$N(R$^{12}$)$_2$;
C(=O)R$^{12}$; CO$_2$R$^{12}$; C(=O)N(R$^{12}$)$_2$; C(=O)NR$^{12}$OR$^{12}$; and CN;

$R^{12}$ is independently selected at each occurence from the group consisting of:
hydrogen;
$C_1$–$C_8$ alkyl;
$C_2$–$C_8$ alkenyl;
$C_2$–$C_8$ alkynyl;
$C_3$–$C_8$ cycloalkyl;
$C_6$–$C_{10}$ bicycloalkyl;
phenyl substituted with 0–3 $R^{21}$;
a heterocyclic ring system composed of 5–10 atoms including at least one nitrogen, oxygen or sulfur atom;

$R^{20}$ is independently selected at each occurence from the group consisting of:
$C_1$–$C_5$ alkyl; $C_2$–$C_4$ alkenyl; $C_3$–$C_{10}$ cycloalkyl; $C_3$–$C_6$ cycloalkylmethyl; $C_2$–$C_6$ alkoxyalkyl; —C(=O)NR$^{23}$R$^{24}$; —C(=O)NR$^{23}$OR$^{23}$; CN; —C(=NH)NHR$^{23}$; —CO$_2$R$^{23}$; —C(=O)R$^{23}$; —CSN(R$^{23}$)$_2$;
—OC(=O)R$^{23}$; —OC(=O)OR$^{23}$; —OR$^{23}$; —OC(=O)NR$^{23}$R$^{24}$;
—NR$^{23}$R$^{24}$; —NHC(=NH)NHR$^{23}$; —NR$^{24}$C(=O)R$^{23}$; =NOR$^{24}$; —NR$^{24}$C(=O)OR$^{24}$; —NR$^{23}$C(=O)NR$^{23}$R$^{24}$; —NR$^{24}$SO$_2$NR$^{23}$R$^{24}$; —NR$^{24}$SO$_2$R$^{23}$;
keto; F; Cl; Br; I; NO$_2$;
a $C_5$–$C_{14}$ carbocyclic residue substituted with 0–1 $R^{23}$;
aryl substituted with 0–1 $R^{21}$; or
a heterocyclic ring system substituted with 0–2 $R^{21}$, composed of 5 to 10 atoms including at least one nitrogen, oxygen or sulfur atom;

$R^{21}$, when a substituent on carbon, is independently selected at each occurence from the group consisting of:
phenyl, benzyl, phenethyl, phenoxy, benzyloxy, halogen, hydroxy, nitro, cyano, $C_1$–$C_5$ alkyl, $C_3$–$C_{10}$ cycloalkyl, $C_3$–$C_6$ cycloalkylmethyl, $C_7$–$C_{10}$ arylalkyl, $C_1$–$C_4$ alkoxy, —NR$^{23}$R$^{24}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino; CF$_3$; OR$^{23}$; CHO; CH$_2$OR$^{23}$; CO$_2$R$^{23}$; C(=O)R$^{23}$; or
2-, 3-, or 4-pyridyl; 2- or 3-thienyl; 2- or 3- furyl;

$R^{21}$, when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —NR$^{23}$R$^{24}$, $C_2$–$C_6$ alkoxyalkyl, $C_1$–$C_4$ haloalkyl, $C_1$–$C_4$ alkoxycarbonyl, $C_1$–$C_4$ alkylcarbonyloxy, $C_1$–$C_4$ alkylcarbonyl;
$R^{23}$ is H, phenyl, benzyl or $C_1$–$C_6$ alkyl;
$R^{24}$ is H, phenyl, benzyl or $C_1$–$C_6$ alkyl;
$R^{25}$ is H or CH$_3$.

Further preferred compounds are those compounds of Formula I as described above, wherein:
$X^1$, $X^2$, $X^3$, and $X^4$ are independently CH or N, provided that 0–1 of X are N with the remaining X groups being CH;
$Z^1$, $Z^2$, $Z^3$, and $Z^4$ are independently CH or N, provided that 0–1 of Z are N with the remaining Z groups being CH;
A is sulfur.
Y is oxygen.
$R^1$, $R^2$, $R^3$, $R^4$, $R^5$, and $R^6$ are independently selected from the following groups:
hydrogen;
$C_1$–$C_8$ alkyl substituted with 0–1 $R^{20}$;
$C_2$–$C_8$ alkenyl;
$C_2$–$C_8$ alkynyl;
$C_3$–$C_8$ cycloalkyl;
$C_6$–$C_{10}$ bicycloalkyl;
phenyl substituted with 0–1 $R^{21}$;
a heterocyclic ring system selected from the group consisting of pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl;
F; Cl; Br; I; NO$_2$;
OR$^{12}$;
N(R$^{12}$)$_2$; NR$^{12}$C(=O)R$^{12}$; NR$^{12}$C(=O)OR$^{12}$; NR$^{12}$SO$_2$R$^{12}$; NR$^{12}$C(=O)N(R$^{12}$)$_2$;
S(O)R$^{12}$; SO$_2$R$^{12}$; SO$_2$N(R$^{12}$)$_2$;
C(=O)R$^{12}$; CO$_2$R$^{12}$; C(=O)N(R$^{12}$)$_2$; C(=O)NR$^{12}$OR$^{12}$; and CN;

$R^1$ and $R^2$, when on adjacent carbon atoms, may alternatively be taken together to form —OCH$_2$O— or —OCH$_2$CH$_2$O—;

$R^7$ is selected from the following groups:
hydrogen;
$C_1$–$C_8$ alkyl substituted with 0–1 $R^{20}$;
$C_2$–$C_8$ alkenyl;
$C_2$–$C_8$ alkynyl;
$C_3$–$C_8$ cycloalkyl;
$C_6$–$C_{10}$ bicycloalkyl;
phenyl substituted with 0–1 $R^{21}$;
a heterocyclic ring system selected from the group consisting of pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl;
F; Cl; Br; I; NO$_2$;
OR$^{12}$;

$N(R^{12})_2$; $NR^{12}C(=O)R^{12}$; $NR^{12}C(=O)OR^{12}$; $NR^{12}SO_2R^{12}$; $NR^{12}C(=O)N(R^{12})_2$;
$S(O)R^{12}$; $SO_2R^{12}$; $SO_2N(R^{12})_2$;
$C(=O)R^{12}$; $CO_2R^{12}$; $C(=O)N(R^{12})_2$; $C(=O)NR^{12}OR^{12}$; and CN;

$R^{12}$ is independently selected at each occurence from the group consisting of:
hydrogen;
$C_1$-$C_8$ alkyl;
$C_2$-$C_8$ alkenyl;
$C_2$-$C_8$ alkynyl;
$C_3$-$C_8$ cycloalkyl;
$C_6$-$C_{10}$ bicycloalkyl;
phenyl substituted with 0-3 $R^{21}$;
a heterocyclic ring system selected from the group consisting of pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl;

$R^{20}$ is independently selected at each occurence from the group consisting of:
$C_1$-$C_5$ alkyl; $C_2$-$C_4$ alkenyl; $C_3$-$C_{10}$ cycloalkyl; $C_3$-$C_6$ cycloalkylmethyl; $C_2$-$C_6$ alkoxyalkyl; $-C(=O)NR^{23}R^{24}$; $-C(=O)NR^{23}OR^{23}$; CN; $-C(=NH)NHR^{23}$; $-CO_2R^{23}$; $-C(=O)R^{23}$; $-CSN(R^{23})_2$;
$-OC(=O)R^{23}$; $-OC(=O)OR^{23}$; $-OR^{23}$; $-OC(=O)NR^{23}R^{24}$; $-NR^{23}R^{24}$; $-NHC(=NH)NHR^{23}$; $-NR^{24}C(=O)R^{23}$; $=NOR^{24}$; $-NR^{24}C(=O)OR^{24}$; $-NR^{23}C(=O)NR^{23}R^{24}$; $-NR^{24}SO_2NR^{23}R^{24}$; $-NR^{24}SO_2R^{23}$;
keto; F; Cl; Br; I; $NO_2$;
a $C_5$-$C_{14}$ carbocyclic residue substituted with 0-1 $R^{23}$; aryl substituted with 0-1 $R^{21}$; or
a heterocyclic ring system selected from the group consisting of pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl;

$R^{21}$, when a substituent on carbon, is independently selected at each occurence from the group consisting of:
phenyl, benzyl, phenethyl, phenoxy, benzyloxy, halogen, hydroxy, nitro, cyano, $C_1$-$C_5$ alkyl, $C_3$-$C_{10}$ cycloalkyl, $-NR^{23}R^{24}$, $CF_3$, $OR^{23}$, CHO, $CH_2OR^{23}$, $CO_2R^{23}$, $C(=O)R^{23}$,
2-, 3-, or 4-pyridyl, 2- or 3-thienyl, 2- or 3- furyl;

$R^{21}$, when a substituent on nitrogen, is selected from one or more of the following:
phenyl, benzyl, phenethyl, hydroxy, $C_1$-$C_4$ hydroxyalkyl $C_1$-$C_4$ alkoxy, $C_1$-$C_4$ alkyl, $C_3$-$C_6$ cycloalkyl, $C_3$-$C_6$ cycloalkylmethyl, $-NR^{23}R^{24}$, $C_2$-$C_6$ alkoxyalkyl, $C_1$-$C_4$ haloalkyl, $C_1$-$C_4$ alkoxycarbonyl, $C_1$-$C_4$ alkylcarbonyloxy, $C_1$-$C_4$ alkylcarbonyl;
$R^{23}$ is H, phenyl, benzyl or $C_1$-$C_6$ alkyl;
$R^{24}$ is H or $C_1$-$C_4$ alkyl;
$R^{25}$ is H or $CH_3$.

More further preferred are compounds of Formula I wherein:

$X^1$, $X^2$, $X^3$, and $X^4$ are independently CH or N, provided that 0-1 of X are N with the remaining X groups being CH;
$Z^1$, $Z^2$, $Z^3$, and $Z^4$ are independently CH or N, provided that 0-1 of Z are N with the remaining Z groups being CH;
A is sulfur;
Y is oxygen;
$R^1$, $R^2$, $R^3$, $R^4$, $R^5$, and $R^6$ are independently selected from the group consisting of: hydrogen, $OCH_3$, halogen, $CH_3$ or $NO_2$; and
$R^7$ is H In the present invention it has been discovered that the compounds of Formula I above are useful as antiinflammatory agents for the treatment and prevention of inflammatory diseases including, but not limited to, rheumatoid and osteoarthritis. The compounds of the present invention are particularly useful for the treatment of rheumatoid and osteoarthritis. Also provided are pharmaceutical compositions containing compounds of Formula I as described above.

The present invention also provides methods for the treatment of inflammatory diseases, including rheumatoid and osteoarthritis, by administering to a host suffering from such inflammatory disease a pharmaceutically effective amount of a compound of Formula I as described above.

Preferred compositions containing compounds of Formula I and methods of using compounds of Formula I as antiinflammatory agents are those compositions and methods suitable for the treatment and prevention of inflammatory diseases including, but not limited to, osteoarthritis and rheumatoid arthritis. In some cases this will involve preventing the underlying cause of the disease state and in other cases, while the underlying disease will not be prevented or cured, it may be reduced in severity or extent and its symptoms ameliorated by the compounds of this invention.

The compounds herein described may have asymmetric centers. All chiral, enantiomeric, diastereomeric, and racemic forms are included in the present invention. Thus, the compounds of Formula I may be provided in the form of an individual stereoisomer, a non-racemic stereoisomer mixture, or a racemic mixture.

Many geometric isomers of olefins, C=N double bonds, and the like can also be present in the compounds described herein, and all such stable isomers are contemplated in the present invention.

When any variable (for example, $R^{12}$, $R^{20}$, $R^{21}$, $R^{23}$, $R^{24}$, and $R^{25}$) occurs more than one time in any constituent or in Formula I, or any other formula herein, its definition on each occurrence is independent of its definition at every other occurrence. Also, combinations of substituents and/or variables are permissible only if such combinations result in stable compounds.

As used herein, "alkyl" is intended to include both branched and straight-chain saturated aliphatic hydrocarbon groups having the specified number of carbon atoms. The number of carbon atoms in a group is specified herein, for example, as $C_1$-$C_5$ to indicate 1-5 carbon atoms. As used herein "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like. "Halo" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; "carbocyclic" is intended to mean any stable 5- to 7- membered monocyclic or bicyclic or 7- to 14-membered bicyclic or tricyclic carbon ring, any of which may be saturated, partially unsaturated, or aromatic, for example, indanyl or tetrahydronaphthyl (tetralin).

As used herein, the term "heterocycle" is intended to mean a stable 5- to 7- membered monocyclic or bicyclic or 7- to 10-membered bicyclic heterocyclic ring which is either saturated or unsaturated, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl.

The term "substituted", as used herein, means that one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo. to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*. 17th ed., Mack Publishing Company, Easton, Pa., 1985, p. 1418, the disclosure of which is hereby incorporated by reference.

SYNTHESIS

The compounds of Formula I can be prepared using the reactions and techniques described herein. The reactions are usually performed in a solvent appropriate to the reagents and materials employed, and suitable for the transformation being effected. In some cases functional groups on the starting materials may need to be protected by standard protecting groups reported in the chemical literature which are well known to one skilled in the art. In some cases, substituents on the starting materials may be incompatible with some of the reaction conditions required in some of the methods described. Such restrictions to the substituents which are compatible with the reaction conditions will be readily apparent to one skilled in the art and alternative methods described herein must then be used.

Some of the compounds of Formula I may possess one or more chiral carbon atoms, allowing the occurrence of different enantiomers and/or diastereomers. In those cases where enantiomers are possible, the separate enantiomers may be obtained in pure or enantiomerically enriched form either by starting from a single enantiomer of a starting material (in those cases where the starting material also possesses the chiral carbon atom), or by resolution of the racemic mixture using standard methods. Diastereomers may generally also be separated using standard methods such as chromatography or fractional crystallization.

The compounds of Formula I may be converted to acid or alkali addition salts by treatment with a suitable pharmaceutically acceptable acid or alkali, respectively, using standard methods.

The compounds of the present invention may be synthesized using the general synthetic procedures described below. Each of the references cited below are hereby incorporated herein by reference.

Compounds of Formula I may be prepared by the oxidative cyclization of the appropriately substituted 4(1H)-quinolinones of Formula VII:

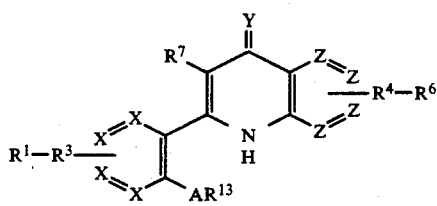

VII in which $R^{13}$ may be H or a suitable protecting group for sulfur or selenium such as benzyl ($CH_2C_6H_5$) or tert-butyl ($CMe_3$) as are known in the chemical literature (Greene, Protective Groups in Organic Synthesis Wiley, New York, 1981). The oxidative cyclization may be carried out using halogens such as bromine or chlorine, or by the use of a halogenating agent such as thionyl chloride or sulfuryl chloride. In the case where $R^{13}$ is benzyl or tert-butyl, the cyclization may also be carried out by oxidation of the sulfide to the corresponding sulfoxide, and treatment of the sulfoxide with a an activated acid derivative such as an acid chloride or acid anhydride. In the case where $R^{13}$ is tert-butyl, the cyclization may also be carried out by oxidation of the sulfide to the corresponding sulfoxide, and heating of the sulfoxide to eliminate isobutene and water. The oxidative cyclization reactions are usually conducted at temperatures in the range from $-15°$ C. to $110°$ C., with the choice of temperature depending upon which particular cyclization method is employed. The cyclization reactions are advantageously conducted in an inert organic solvent such as dichloromethane, benzene or chloroform. When halogens or halogenating agents are employed, the addition of a proton acceptor is often beneficial, with triethylamine, pyridine, and 1,4-diazabicyclo[2.2.2]octane being especially suitable.

The substituted 4(1H)-quinolinones of Formula VII may be prepared by condensation of an appropriately substituted aldehyde of Formula XIII with a suitably functionalized β-ketosulfoxide of

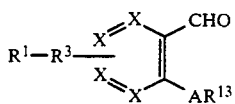

XIII

Formula XIV according to the method of von Strandtmann (J. Heterocyclic Chem. (1972) 9: 173).

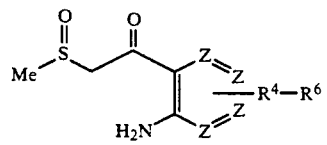

XIV

The preparation of compounds of Formula VII, shown in Scheme 1, serves to illustrate the method. Thus, a mixture of an aldehyde of Formula XIII, a β-ketosulfoxide of Formula XIV, and a catalytic amount of a secondary amine base, such as piperidine, in an inert solvent such as benzene or toluene, is heated at the boiling point of the solvent for an appropriate amount of time to afford a substituted 4(1H)-quinolinone of Formula VII.

Scheme 1

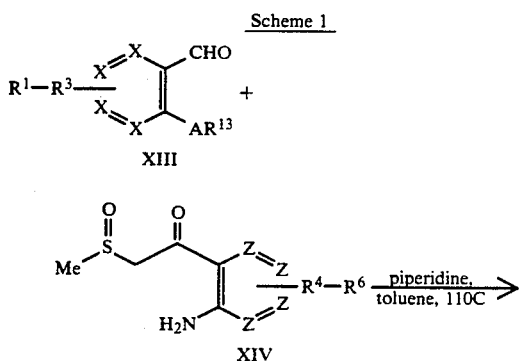

-continued
Scheme 1

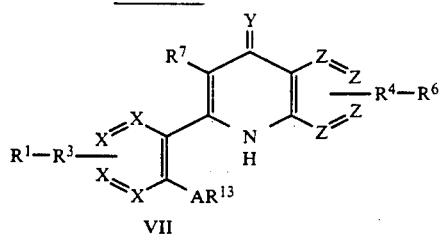

VII

The required aldehydes of Formula XIII may be prepared by known literature procedures, for example by the procedure of Stacy (J. Org. Chem. (1970) 35: 3495), or by manipulation of an appropriately functionalized thio- or selenosalicylic acid derivative, as shown in Scheme 2. Thus, a suitably functionalized thio- or selenosalicylic acid is treated with an excess amount of an alkylating agent, in particular with benzyl bromide, in the presence of a suitable base, such as potassium carbonate, in a neutral solvent such as acetone or 2-butanone at the boiling point of the solvent. In this way the carboxylic acid group is converted to the corresponding alkyl or benzyl ester, and the thiol or selenol is converted to the corresponding alkyl or benzyl sulfide or selenide, respectively. The ester group is then reduced to the corresponding benzyllic alcohol with an appropriate reducing agent, usually lithium aluminum hydride, in a inert solvent such as diethyl ether or tetrahydrofuran. Oxidation of the resulting benzyllic alcohol to the corresponding aldehyde is accomplished by a suitable method, usually by the procedure of Swern (Synthesis (1981) 165).

Scheme 2

The required aldehydes of Formula XIII may also be prepared using directed metallation methodology, which is well-known in the literature and has been reviewed in Organic Reactions (1979) 26: 1, and in Synthesis (1983) 957. The method is illustrated in Scheme 3. Thus, a suitable aromatic aldehyde is converted to a dialkyl acetal, wherein R14 is usually methyl or ethyl, using standard methods. The resulting aromatic acetal is lithiated ortho to the acetal group, usually by treatment with an alkyllithium reagent, such as n-butyllithium, sec-butyllithium, or tert-butyllithium, in an ethereal solvent such as diethyl ether or tetrahydrofuran, at temperatures from $-78°$ C. to $25°$ C. The resulting ortho-lithio acetal is treated in the same flask without isolation with a compound of the formula $R^{13}AAR^{13}$ or $R^{13}ACN$, usually at temperatures from $-78°$ C. to $25°$ C., to afford the corresponding dialkyl acetal precursor of aldehydes of formula XIII. Hydrolysis of the acetal moiety with water in the presence of an acid source, such as hydrochloric acid or p-toluenesulfonic acid, in a suitable solvent, such as acetone or tetrahydrofuran, provides compounds of Formula XIII.

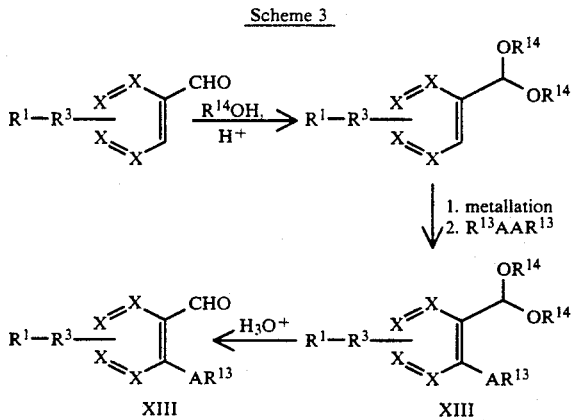

Scheme 3

The β-ketosulfoxides of Formulas XIV-XIX are prepared from suitably functionalized isatoic anhydrides, or from the esters of suitably functionalized anthranilic acids, by the literature procedure reported by von Strandtmann (J. cyclic Chem. (1972) 9: 173). The required isatoic anhydrides and anthranilic acid esters are either offered commercially, or can be prepared from available precursors by standard methods known to those of skill in the art. The preparation of β-ketosulfoxides of the Formula XIV, shown in Scheme 4, serves to illustrate the procedure. Thus, a suitably functionalized isatoic anhydride or anthranilic acid ester is treated with the sodium salt of dimethyl sulfoxide in a mixture of dimethylsulfoxide and a suitable neutral solvent, usually benzene or toluene, at 0° C. to 40° C., to provide the β-ketosulfoxides of Formula XIV. The sodium salt of dimethylsulfoxide is prepared by standard methods familiar to those of skill in the art.

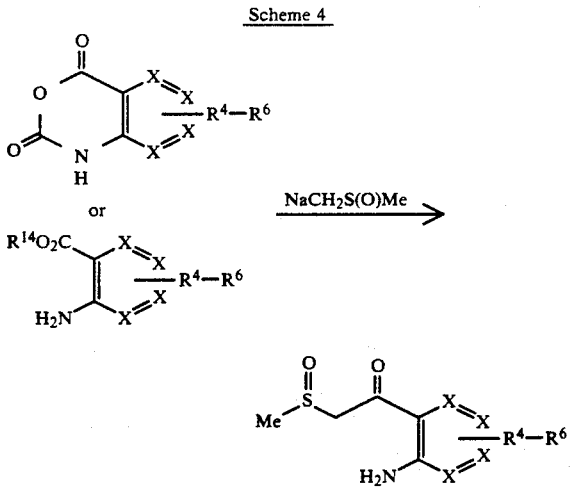

Scheme 4

Compounds of Formula I wherein Y is sulfur are readily prepared from compounds of Formula I in which Y is oxygen by treatment of the starting material (Y=O) with a thiating reagent, such as phosphorous pentasulfide or preferably 2,4-bis-(4-methoxyphenyl)-2,4-dithiono-1,3,2,4-dithiadiphosphetane ("Lawesson's reagent"). Both reagents are offered commercially. The reaction is most often carried out in an inert organic solvent such as benzene, toluene, or xylene, and usually at the boiling point of the solvent.

Certain substituents in compounds of Formula I wherein $R^n$ is other than H may be prepared from other compounds of Formula I by standard chemical manipulations which are well known to one skilled in the art. In certain instances it may be advantageous to carry out the synthetic steps represented in Schemes 1-4 in an order different from the order represented in the Schemes; in these cases the advantage of rearranging the steps and the appropriate ordering of the synthetic steps will be readily apparent to one skilled in the art.

Examples of the preparation of 5H-[1,2]benzisothiazolo[2,3-a]quinoline-5-ones are given below. All reactions were performed under an atmosphere of dry nitrogen. Nuclear magnetic resonance (NMR) spectra were obtained at a field strength of 300 MHz; abbreviations for NMR data are as follows: s=singlet, d=doublet, t= triplet, q=quartet, m=multiplet, app=apparent, br=broad, CDCl$_3$=deuterochloroform solvent, DMSO−d$_6$=hexadeuterodimethylsulfoxide solvent. Peak positions for NMR data are reported as parts per million downfield from the internal standard tetramethylsilane. Mass spectra were obtained by chemical ionization techniques using either ammonia or methane as the reagent gas.

EXAMPLE 1

2-(Phenylmethyl)thio]benzaldehyde

Step 1: Thiosalicylic acid (15.42 g, 0.1 mole, 1 equiv.), benzyl bromide (26.2 ml, 0.22 mole, 2.2 equiv.), and anhydrous potassium carbonate (34.55 g, 0.25 mole, 2.5 equiv.) were combined in 2-butanone (500 ml), and the mixture was heated to reflux. After 14.5 hr, the reaction was concentrated to dryness and the residue was diluted with water (200 ml). CH$_2$Cl$_2$ extraction (3×200 ml), drying (MgSO$_4$), and concentration gave a light yellow solid. This was used without further purification: TLC (1:1 benzene/hexanes) R$_f$ 0.41; $^1$H NMR (CDCl$_3$) δ8.00 (br d, 1 H), 7.20–7.53 (m, 12 H), 7.10–7.20 (m, 1 H), 5.35 (s, 2 H), 4.15 (s, 2 H).

Step 2: Lithium aluminum hydride (4.17 g, 0.11 mole, 1.1 equiv.) was added portionwise to a suspension of the product of Step 1 (0.1 mole, 1 equiv.)) in THF (200 ml) at 0° C. After 5 min, the reaction was warmed to 25° C. and stirred for 15 min. EtOAc was added to decompose excess hydride, then the cloudy yellow solution was concentrated to dryness. The yellow residue was partitioned between 1.0 N HCl (200 ml) and CH$_2$Cl$_2$ (200 ml), and the layers were separated. CH$_2$Cl$_2$ extraction (2×200 ml), drying (MgSO$_4$), concentration, and silica gel chromatography (5% EtOAc/benzene) gave the product as a yellow oil which solidified (23.27 g, quantitative): TLC (5% EtOAc/benzene) R$_f$ 0.43; $^1$H NMR (CDCl$_3$) δ7.31–7.45 (m, 3 H), 7.15–7.31 (m, 6 H), 4.62 (d, J=7 Hz, 2 H), 4.07 (s, 2 H), 1.93 (br t, 1 H).

Step 3: A solution of dry DMSO (18 ml, 0.25 mole, 2.5 equiv.) in dry CH$_2$Cl$_2$ (45 ml) was added dropwise over 25 min to a solution of oxalyl chloride (10.5 ml, 0.12 mole, 1.2 equiv.) in dry CH$_2$Cl$_2$ (530 ml) in a flame - dried flask at −78° C. The clear, colorless solution was stirred at that temperature for 15 min, then a solution of the product from Step 2 (0.1 mole, 1 equiv.) in dry CH$_2$Cl$_2$ (50 ml) was added dropwise over 20 min. The cloudy solution was stirred at −78° C. for 0.5 hr, then triethylamine (49 ml, 0.35 mole, 3.5 equiv.) was added over 1 min. The cold bath was removed and the reaction was allowed to warm for 45 min. The resulting mixture was diluted with benzene (500 ml) and filtered through a pad of silica gel. Concentration of the filtrate gave a yellow oil which solidified. Silica gel chromatography (2:1 benzene/hexanes) gave 2-[(phenylmethyl)thio]benzaldehyde (19.32 g, 85% for three steps) as a pale yellow solid: mp 74–75.5 ° C.; TLC (1:1 benzene/hexanes) R$_f$ 0.35; 1H NMR (CDCl$_3$) δ10.25 (s, 1 H), 7.81 (app d, 1 H), 7.41–7.53 (m, 3 H), 7.18–7.38 (m, 7 H), 4.13 (s, 2 H); IR (KBr) 1692, 1586, 1460, 1196, 750, 712, 698 cm$^{-1}$; MS (CH$_4$), m/e 257.1 (M+C$_2$H$_5$)$^+$, 229.1 (M+H)$^+$.

EXAMPLE 2

2-(Phenylmethyl)thioloyridine-3-carboxaldehyde

Step 1: 2-Mercaptonicotinic acid (20.2 g, 0.13 mole, 1 equiv.), benzyl bromide (34 ml, 0.29 mole, 2.2 equiv.), and anhydrous potassium carbonate (44.9 g, 0.33 mole, 2.5 equiv.) were combined in 2-butanone (750 ml), and the mixture was heated to reflux. After 2 hr, the reaction was cooled to RT and filtered, and the filter cake was washed thoroughly with CHCl$_3$. Concentration of the combined filtrate and washings gave the product (52.19 g) as a light brown solid. This was used without further purification: TLC (CHCl$_3$) R$_f$ 0.39; 1H NMR (CDCl$_3$) δ8.58 (app dd, 1 H), 8.23 (app dd, 1 H), 7.15–7.52 (m, 10 H), 7.05 (dd, J=9, 6 Hz, 1 H) 5.34 (s, 2 H), 4.43 (s, 2 H).

Step 2: Lithium aluminum hydride (5.43 g, 0.14 mole, 1.1 equiv.) was added portionwise to a suspension of the product of Step 1 (0.13 mole, 1 equiv.) in THF (600 ml) at 0° C. After 5 min, the reaction was warmed to 25° C. and stirred for 15 min. The reaction was then concentrated and the residue was partitioned between 1.0 N HCl and CH$_2$Cl$_2$. The layers were separated and the organic layer was washed sequentially with saturated aqueous NaHCO$_3$ and brine. Drying (MgSO$_4$), and concentration gave a dark brown oil which was chromatographed on silica gel (10% EtOAc/CHCl$_3$). The product (37.0 g, quantitative) was obtained as an orange oil: TLC (20% EtOAc/CHCl$_3$) R$_f$ 0.42; 1H NMR (CDCl$_3$) δ8.40 (br d, 1 H), 7.62 (br d, 1 H), 7.17–7.45 (m, 5 H), 7.05 (dd, J=9, 6 Hz, 1 H), 4.63 (d, J=7 Hz, 2 H), 4.50 (s, 2 H), 2.09 (br t, 1 H).

Step 3: A solution of dry DMSO (29.1 ml, 0.41 mole, 3.2 equiv.) in dry CH$_2$C$_2$ (100 ml) was added dropwise over 10 min to a solution of oxalyl chloride (17.2 ml, 0.20 mole, 1.5 equiv.) in dry CH$_2$Cl$_2$ (1000 ml) in a flame-dried flask at −78° C. The clear, colorless solution was stirred at that temperature for 15 min, then a solution of the product from Step 2 (0.13 mole, 1 equiv.) in dry CH$_2$Cl$_2$ (100 ml) was added dropwise over 10 min. The cloudy solution was stirred at −78° C. for 0.5 hr, then triethylamine (80 ml, 0.57 mole, 4.4 equiv.) was added. The cold bath was removed and the reaction was allowed to warm to RT. The resulting mixture was washed sequentially with H$_2$O (3×), saturated aqueous NaHCO$_3$ (1×), and brine (1×). Drying (MgSO$_4$) and concentration gave a brown solid. Silica gel chromatography (CHCl$_3$) gave 2-[(phenylmethyl)thio]pyridine-3-carboxaldehyde (22.76 g, 76% for three steps) as a yellow solid: mp 71.5–73° C.; TLC (CHCl$_3$) R$_f$ 0.40; 1H NMR (CDCl$_3$) δ10.20 (s, 1 H), 8.61 (app dd, 1 H), 7.98 (app dd, 1 H), 7.38–7.48 (m, 2 H), 7.12–7.38 (m, 4 H), 4.51 (s, 2 H); IR (KBr) 1687, 1578, 1547, 1374 cm$^{-1}$; MS (NH$_3$), m/e (%) 230.2 (100, (M+H)$^+$).

EXAMPLE 3

3-Methoxy-2-(phenylmethyl)thiolbenzaldehyde

Step 1: p-Toluenesulfonic acid monohydrate (3.80 g, 0.02 mmole, 0.1 equiv.) was added all at once to a solution of m-anisaldehyde (24.3 ml, 0.20 mole, 1 equiv.) and trimethylorthoformate (66 ml, 0.60 mole, 3 equiv.) in MeOH (110 ml) at 0° C. After 0.5 hr, the solution was poured into hexanes (500 ml) and washed with saturated aqueous NaHCO$_3$ (2 ×100 ml). The combined aqueous layers were back-extracted with hexanes (1×100 ml), and the combined organic layers were dried (Na$_2$SO$_4$) and concentrated to a light yellow liquid (approximately 30 ml). Distillation under reduced pressure gave the product (29.37 g, 81%) as a colorless liquid: bp 87 −90° C. (2.4 mmHg); TLC (10% EtOAc/hexanes) R$_f$ 0.44; 1H NMR (CDCl$_3$) δ7.28 (app t, 1 H), 7.00–7.06 (m, 2 H), 6.83–6.91 (br dd, 1H), 5.36 (s, 1H), 3.82 (s, 3 H), 3.34 (s, 6 H).

Step 2: A solution of tert-BuLi in pentane (1.7 M, 17.6 ml, 30 mmole, 1 equiv.) was added dropwise over 10 min to a solution of the product of Step 1 (5.47 g, 30 mmole, 1 equiv.) in dry Et$_2$O (60 ml) in a flame-dried flask at 0° C. The reaction was allowed to stir at 0° C. to RT for 4 hr. The resulting dark, heterogeneous mixture was cooled to −78° C., and a solution of dibenzyl disulfide (7.39 g, 30 mmole, 1 equiv.) in dry Et$_2$O (60 ml) was added over 2 min. The mixture was warmed to RT and stirred for 3 hr, during which time the color gradually changed to yellow. The reaction was then washed with H$_2$O (3×50 ml), dried (MgSO$_4$), and concentrated. Silica gel chromatography (1% EtOAc/benzene) gave the product (3.67 g, 40%) as a yellow oil: TLC (benzene) R$_f$ 0.29; 1H NMR (CDCl$_3$) δ7.23–7.37 (m, 1 H), 7.10–7.23 (m 4 H), 7.03–7.10 (m 2 H), 6.89 (br dd, 1 H), 5.47 (s, 1 H), 3.98 (s, 2 H), 3.92 (s, 3 H), 3.20 (s, 6 H).

Step 3: A solution of the product of Step 2 (3.61 g, 11.9 mmole, 1 equiv.) and p-toluenesulfonic acid monohydrate (453 mg, 2.38 mmole, 0.2 equiv.) in acetone/H$_2$O (9:1) (60 ml) was stirred at RT for 6 hr. The resulting solution was diluted with Et$_2$O (250 ml) and washed with saturated aqueous NaHCO$_3$ (2×50 ml). Drying (MgSO$_4$), concentration, and silica gel chromatography (benzene) gave 3-methoxy-2-[(phenylmethyl)-thio]benzaldehyde (2.67 g, 87%) as a yellow oil: TLC (benzene) R$_f$ 0.57; 1H NMR (CDCl$_3$) δ10.33 (s, 1 H), 7.33–7.48 (m, 2 H), 7.05–7.13 (m, 4 H), 6.95–7.05 (m, 2 H), 4.02 (s, 2 H), 3.98 (s, 3 H); IR (KBr plate) 1692, 1571, 1464, 1267, 1237, 1063, 700 cm$^{-1}$; MS (NH$_3$), m/e (%) 276.0 (52, (M+NH$_4$)$^+$), 259.0 (100, (M+H)$^+$).

EXAMPLE 4

1-(2-Aminophenyl)-2-(methylsulfinyl)ethanone

This was prepared by modification of the procedures reported in the literature (J. Heterocyclic Chem. (1972) 9:173).

From isatoic anhydride: Sodium hydride (18 g, 0.75 mole, 3 equiv.) was added portionwise over 45 min to dry DMSO (375 ml) at 65–70° C. The mixture was kept at that temperature for another 1 hr, then was cooled to +15° C. A solution of isatoic anhydride (40.78 g, 0.25 mole, 1 equiv.) in DMSO (150 ml) was added in portions such that the internal temperature did not exceed 30° C., and the resulting dark mixture was stirred at RT for 0.5 hr, then at 40-45° C. for 1 hr. The reaction was then poured into ice/H$_2$O (2000 ml), and the mixture was carefully acidified with concentrated HCl to pH 2. CH$_2$Cl$_2$ extraction, drying (MgSO$_4$), and concentration gave a brown oil. Silica gel chromatography (5% MeOH/EtOAc) gave the product as an orange oil which solidified. Recrystallization from EtOAc-BuCl gave 1-(2-aminophenyl)-2-(methylsulfinyl)ethanone (12.7 g, 26%) as a yellow solid: mp 99-100.5° C. (Lit. 100-102° C.); TLC (3%MeOH/EtOAc) R$_f$ 0.41; 1H NMR (CDCl$_3$) δ7.66 (dd, J=8.4, 1.1 Hz, 1 H), 7.31 (m, 1 H), 6.68 (m, 2 H), 6.39 (br s, 2 H), 4.53 (d, J=14.3 Hz, 1 H), 4.23 (d, J=14.3 Hz, 1 H), 2.76 (s, 3 H); IR (KBr) 3440, 3300, 1640, 1587, 1548, 1029 cm$^{-1}$; MS (NH$_3$), m/e (%) 215.2 (100, (M+NH$_4$)+), 198.2 (84.6, (M+H)+; ).

From ethyl anthranilate: A mixture of sodium hydride (60% dispersion in mineral oil, 24.00 g, 0.6 mole, 3 equiv.), dry DMSO (71.0 ml, 1.0 mole, 5 equiv.), and benzene (130 ml) was heated at 80° C. until gas evolution ceased (1.5 hr), then was cooled in ice/H$_2$O. A solution of ethyl anthranilate (29.6 ml, 0.2 mole, 1 equiv.) in benzene (100 ml) was added at a rate such that the internal temperature did not exceed 25° C., and the mixture was stirred for 0.5 hr. The reaction was poured into ice/H$_2$O and the pH was adjusted to 5-6 with concentrated HCl. EtOAc extraction, drying (MgSO$_4$) and concentration gave a cloudy, orange oil. Silica gel chromatography (3% MeOH/EtOAc, then 5% MeOH/EtOAc) gave 1-(2-aminophenyl)-2-(methylsulfinyl)ethanone (23.43 g, 59%) as a yellow solid. Material prepared in this way was identical to that prepared from isatoic anhydride.

The compounds of Examples 5-7 were prepared using the appropriate compounds and reagents by procedures analogous to those of Example 4.

EXAMPLE 5

1-(2-Amino-5-chlorophenyl)-2-(methylsulfinyl)ethanone mp 135-139° C. (dec) (Lit. (J. Heterocyclic Chem. (1972) 9: 173) 143-145° C.); TLC (3% MeOH/EtOAc) R$_f$ 0.53; 1H NMR (CDCl$_3$) δ7.61 (d, J=2.2 Hz, 1 H), 7.25 (dd, J=9.1, 2.2 Hz, 1 H), 6.64 (d, J=9.1 Hz, 1 H), 6.45 (br s, 1 H), 4.43 (d, J=14.5 Hz, 1 H), 4.22 (d, J=14.5 Hz, 1 H), 2.76 (s, 3 H); IR (KBr) 3430, 3310, 1646, 1618, 1030 cm$^{-1}$; MS (NH$_3$), m/e (%) 249.2 (100, (M+NH$_4$)+), 232.2 (59, (M+H)+), 232.2 (59).

EXAMPLE 6

1-(2-Amino-3-methoxyphenyl)-2-(methylsulfinyl)ethanone mp 106-108° C.; TLC (5% MeOH/EtOAc) R$_f$ 0.28; 1H NMR (CDCl$_3$) δ7.27 (app d, 1 H), 6.87 (d, J=7.7 Hz, 1 H), 6.73 (br s, 2 H), 6.61 (t, J=8.1 Hz, 1 H), 4.56 (d, J=14.3 Hz, 1 H), 4.23 (d, J=14.3 Hz, 1 H), 3.88 (s, 3 H), 2.75 (s, 3 H); IR (KBr) 3488, 3366, 1636, 1616, 1548, 1456, 1228, 1040 cm$^{-1}$; MS (NH$_3$), m/e (%) 245.1 (22.9, (M+NH$_4$)+), 227.9 (100, (M+H)+).

EXAMPLE 7

1-(2-Amino-3,4,5-trimethoxyphenyl)-2-(methylsulfinyl)ethanone mp 102-104° C.; TLC (10% MeOH/EtOAc) R$_f$ 0.48; 1H NMR (CDCl$_3$) d 6.91 (s, 1 H), 6.49 (br s, 2 H), 4.45 (d, J=14.2 Hz, 1 H), 4.20 (d, J=14.2 Hz, 1 H), 3.99 (s, 3 H), 3.86 (s, 3 H), 3.83 (s, 3 H), 2.76 (s, 3 H); IR (KBr) 3424, 3306, 1630, 1589, 1538, 1496, 1442, 1424, 1389, 1318, 1281, 1253, 1201, 1146, 1090, 1034, 1004, 963, cm$^{-1}$; MS (NH$_3$-CI/DDIP), m/e (%) 288.2 (100, (M+H)+), 226.2 (16.6).

EXAMPLE 8

2-2-(Phenylmethyl)thiolphenyl]-4(1H)-quinolinone

2-[(Phenylmethyl)thio]benzaldehyde (2.28 g, 10 mmole, 1 equiv.), 1-(2-aminophenyl)-2-(methylsulfinyl)ethanone (1.97 g, 10 mmole, 1 equiv.), and piperidine (0.5 ml, 5 mmole, 0.5 equiv.) were combined in toluene (50 ml), and the mixture was heated to reflux under a Dean-Stark trap. After 3 hr, the reaction was concentrated and the residue was chromatographed on silica gel (50% EtOAc/CHCl$_3$) to afford 2-[2-[(phenylmethyl)thio]phenyl]-4(1H)-quinolinone (1.90 g, 55%) as a brownish-yellow foam. Recrystallization from CHCl$_3$/EtOAc gave light yellow crystals (1.39 g): mp 196-197° C.; TLC (50% EtOAc/CHCl$_3$) R$_f$ 0.31; 1H NMR (CDCl$_3$) δ8.63 (br s, 1 H), 8.36 (dd, J=8.1, 0.8 Hz, 1 H), 7.50-7.62 (m, 2 H), 7.28-7.45 (m, 4 H), 7.16-7.26 (m, 4 H), 7.00-7.08 (m, 2 H), 6.24 (d, J=1.8 Hz, 1 H), 3.97 (s, 2 H); IR (KBr) 2100-3200 (br), 1632, 1594, 1530, 1497, 1439 cm$^{-1}$; MS (NH$_3$), m/e (%) 344.1 (100, (M+H)+), 254.2 (26.9). Anal. Calcd for C$_{22}$H$_{17}$NOS: C, 76.54; H, 4.87; N, 3.91; S, 9.12. Found: C, 76.94; H, 4.99; N, 4.08; S, 9.34.

The compounds of Examples 9-12 were prepared using appropriate reagents and compounds by methods analogous to those used for Example 8:

EXAMPLE 9

6-Chloro-2-2-(phenylmethyl)thiophenyl]-4(1H)-quinolinone mp 198.5-201.5° C (from CHCl$_3$/EtOAc); TLC (50% EtOAc/CHCl$_3$) R$_f$ 0.58; 1H NMR (CDCl$_3$) δ9.08 (br s, 1 H), 8.28 (m, 1 H), 7.45-7.58 (m, 2 H), 7.13-7.40 (m, 7 H), 6.97-7.10 (m, 2 H), 6.15 (d, J=1.8 Hz, 1 H), 3.96 (s, 2 H); IR (KBr) 2100-3400 (br), 1630, 1593, 1579, 1564, 1552, 1533, 1492 cm$^{-1}$; MS (NH$_3$), m/e (%) 380.1 (40, ($^{37}$Cl M+H)+), 378.1 (100, ($^{35}$Cl M+H)+), 288.2 (27.5). Anal. Calcd for C$_{22}$H$_{16}$ClNOS: C, 69.93; H, 4.27; Cl, 9.38; N, 3.71; S, 8.48. Found: C, 69.82; H, 4.09; Cl, 9.61; N, 3.57; S, 8.28.

EXAMPLE 10

8-Methoxy-2-2-[(phenylmethyl)thiolphenyl]-4(1H)-quinolinone mp 139-140.5° C. (from EtOAc/hexanes); TLC (50% EtOAc/CHCl$_3$) R$_f$ 0.27; 1H NMR (CDCl$_3$) δ9.13 (br s, 1 H), 7.96 (d, J=8.4 Hz, 1 H), 7.05-7.50 (m, 11 H), 6.36 (d, J=2.2 Hz, 1 H), 3.99 (s, 3 H), 3.97 (s, 2 H); IR (KBr) 2300-3700 (br), 1632, 1596, 1578, 1547, 1507, 1264 cm$^{-1}$; MS (NH$_3$), m/e (%) 374.1 (100, (M+H)+); Anal. Calcd for C$_{23}$H$_{19}$NO$_2$S: C, 73.97; H, 5.13; N, 3.75; S, 8.59. Found: C, 73.78; H, 5.01; N, 3.64; S, 8.56.

EXAMPLE 11

2-2-(Phenylmethyl)thiolphenyl]-6,7,8-trimethoxy-4(1H)-quinolinone

TLC (5% MeOH in 50% EtOAc/CHCl$_3$) R$_f$ 0.50; 1H NMR (CDCl$_3$) δ9.18 (br s, 1 H), 7.55 (s, 1 H), 7.43-7.53 (m, 2 H), 7.32-7.43 (m, 2 H), 7.15-7.23 (m, 2 H), 7.07-7.15 (m, 2 H), 4.02 (s, 3 H), 4.002 (s, 3 H), 3.996 (s, 3 H), 3.96 (s, 3 H); IR (KBr) 2300-3700 (br), 1597, 1579, 1567, 1553, 1476, 1121 cm$^{-1}$; MS (NH$_3$), m/e (%) 434.1 (100, (M+H)$^+$), 344.0 (55).

EXAMPLE 12

2-3-Methoxy-2-(phenylmethyl)thiolphenyl]-4(1H)-quinolinone mp>250° C. (from 1, 2-dichlorobenzene); TLC (2% MeOH in 50% EtOAc/CHCl$_3$) R$_f$ 0.41; $^1$H NMR (CDCl$_3$) δ8.35 (d, J=8.1 Hz, 1 H), 7.50–7.63 (m, 1 H), 7.36–7.46 (m, 1 H), 7.15–7.36 (m, 4 H), 7.08 (dd, J=8.4, 1.1 Hz, 1 H), 6.97 (dd, J=7.7, 1.5 Hz, 1 H), 6.85–6.97 (m, 3 H), 6.08 (d, J=1.8 Hz, 1 H), 4.05 (s, 3 H), 4.01 (s, 2 H); IR (KBr) 2100–3300 (br), 1637, 1596, 1575, 1533, 1495, 1474, 1466, 1439, 1269 cm$^{-1}$; MS [NH$_3$–Cl/DDIP, m/e (%) 374.0 (100, (M+H)$^+$), 284.0 (24.2).

EXAMPLE 13

2-[2-[(Phenylmethyl)thio1-3-pyridinyl]-4(1H)-quinolinone

2-[(Phenylmethyl)thio]pyridine-3-carboxaldehyde (6.01 g, 26.2 mmole, 1 equiv.), 1-(2-aminophenyl)-2-(methylsulfinyl)ethanone (5.17 g, 26.2 mmole, 1 equiv.), and piperidine (1.3 ml, 13.1 mmole, 0.5 equiv.) were combined in toluene (240 ml), and the mixture was heated to reflux under a Dean - Stark trap. After 3.5 hr, the reaction was concentrated to one half volume and cooled in the refrigerator overnight. Filtration of the mixture gave 2-[2-[(phenylmethyl)thio]-3-pyridinyl]-4(1H)-quinolinone (2.37 g, 26%) as a pale yellow solid: mp 219–226 (dec); TLC (50% EtOAc/CHCl$_3$) R$_f$0.19; $^1$H NMR (DMSO-d$_6$) δ11.93 (br s, 1 H), 8.67 (dd, J=4.8, 1.8 Hz, 1 H), 8.10 (dd, J=8.1, 1.1 Hz, 1 H), 7.87 (dd, J=7.7, 1.8 Hz, 1 H), 7.60–7.72 (m, 1 H), 7.58 (d, J=8.0 Hz, 1 H), 7.17–7.45 (m, 7 H), 6.06 (br s, 1 H), 4.44 (s, 2 H); IR (KBr) 2100–3300 (br), 1633, 1595, 1573, 1549, 1534, 1502, 1474, 1440 cm$^{-1}$; MS (NH$_3$), m/e (%) 345.0 (100, (M+H)$^+$), 255.1 (22.7), 253.1 (20.7). Anal. Calcd for C$_{21}$H$_{16}$N$_2$OS: C, 73.23; H, 4.68; N, 8.13; S, 9.31. Found: C, 72.98; H, 4.56; N, 8.03; S, 9.20.

EXAMPLE 14

5H-1.21Benzisothiazolo2.3-a]quinoline-5-one

Sulfuryl chloride (0.255 ml, 3.15 mmole, 1.05 equiv.) was added dropwise over 2 min to a solution of 2-[2-(phenylmethyl)thio]phenyl]-4(1H)-quinolinone (1.03 g, 3 mmole, 1 equiv.) in dry CH$_2$Cl$_2$ (30 ml) at −15° C. The mixture was stirred for 0.5 hr, then 1,4-diazabicyclo[2.2.2]octane (504.8 mg, 4.5 mmole, 1.5 equiv.) was added. Stirring at −15° C. was continued for an additional 10 min, then the mixture was warmed to 25° C. After 0.5 hr at 25° C. the reaction was quenched with 10% aqueous Na$_2$CO$_3$ (30 ml) and extracted with CH$_2$Cl$_2$. Drying (MgSO$_4$), concentration, and silica gel chromatography (10% MeOH in 50% EtOAc/CHCl$_3$) gave 5H-[1,2]benzisothiazolo[2,3-a]quinoline-5-one (0.28 g, 37%) as a yellow solid. Recrystallization from CHCl$_3$/EtOAc gave yellow, very fine needles: mp phase change at 244–245° C., actual mp>300° C.; TLC (10% MeOH in 50% EtOAc/CHCl$_3$) R$_f$0.41; $^1$H NMR (CDCl$_3$) δ8.53 (m, 1 H), 8.00 (app d, 1 H), 7.6–7.8 (m, 3 H), 7.4–7.6 (m, 3 H), 7.09 (s, 1 H); IR (KBr) 1618, 593, 1571, 1544, 1483, 1464, 1445, 748 cm$^{-1}$; MS (NH$_3$), m/e (%) 252.1 (100, (M +H)+). Anal. Calcd for C$_{15}$H$_9$NOS: C, 71.69; H, 3.61; N, 5.57; S, 12.76. Found: C, 71.39; H, 3.51; N, 5.43; S, 12.68.

EXAMPLE 15

3-Chloro-5H-1,21benzisothiazolo[2.3-a]quinoline-5-one

Sulfuryl chloride (0.305 ml, 3.78 mmole, 1.0 equiv.) was added dropwise over 3 min to a suspension of 6-chloro-2-[2-[(phenylmethyl)thio]phenyl]-4(1H)-quinolinone (1.43 g, 3,78 mmole, 1 equiv.) in dry, EtOH-free CHCl$_3$ (190 ml) at −15° C. The mixture was stirred for 0.5 hr, then was heated to reflux. After 20 min, the reaction was cooled to 25° C, and 1,4-diazabicyclo[2.2.-2]octane (636 mg, 5.67 mmole, 1.5 equiv.) was added. The nearly homogeneous solution was stirred at 25° C. for an additional 5 min, then was washed with H$_2$O (3×50 ml). The combined aqueous layers, which contained suspended product, were back - extracted with CHCl$_3$, and the combined organic layers were diluted with CHCl$_3$ (200 ml) and MeOH (50 ml) to dissolve suspended solids. Drying (MgSO$_4$), concentration, and silica gel chromatography (CHCl$_3$, then 10% MeOH in 50% EtOAc/CHCl$_3$, then 10% MeOH/CHCl$_3$) gave 3-chloro-5H-[1,2]benzisothiazolo[2,3-a]quinoline-5-one (0.28 g, 26%) as a yellow solid. Two recrystallizations from CHCl$_3$/EtOAc gave yellow, very fine needles: mp>350° C.; TLC (5% MeOH in 50% EtOAc/CHCl$_3$) R$_f$ 0.32; $^1$H NMR (CDCl$_3$) δ8.52 (d, J=2.2 Hz, 1 H), 8.00 (app d, 1 H), 7.62–7.74 (m, 3 H), 7.50–7.60 (m, 1H), 7.44 (d, J=8.8 Hz, 1 H), 7.08 (s, 1 H); IR (KBr) 1613, 1587, 1567, 1554, 1539, 1461, 1450 cm$^{-1}$; MS (NH$_3$), m/e (%) 288 (41, ($^{37}$Cl M+H)$^+$), 286 (100, ($^{35}$Cl M+H)$^+$). Anal. Calcd for C$_{15}$H$_8$ClNOS: C, 63.05; H, 2.82; N, 4.90. Found: C, 62.83; H, 2.51; N, 4.75.

EXAMPLE 16

1-Methoxy-5H-[1.2]benzisothiazolo[2.3-a]quinoline-5-one

Step 1: 3-Chloroperoxybenzoic acid (70%, 1.09 g, 4.44 mmole, 1.05 equiv.) was added in three portions at 0.5 min intervals to a solution of 8-methoxy-2-[2-[(phenylmethyl)thio]phenyl]-4(1H)-quinolinone (1.58 g, 4.23 mmole, 1.0 equiv.) in CH$_2$Cl$_2$ (85 ml) at 0° C. After 10 min, the solution was washed with 5% aqueous NaHCO$_3$ (3×40 ml). Drying (MgSO$_4$) and concentration gave the crude sulfoxide, which was use without further purification: TLC (5% MeOH in 50% EtOAc/CHCl$_3$) R$_f$0.31; $^1$H NMR (CDCl$_3$) δ9.05 (br s, 1 H), 7.96 (d, J=8.4 Hz, 1 H), 7.80 (m, 1 H), 7.50–7.65 (m, 3 H), 7.33 (t, J=8.1 Hz, 1 H), 7.16–7.27 (m, 1 H), 7.12 (m, 3 H), 6.79 (d, J=7.0 Hz, 2 H), 6.24 (d, J=1.8 Hz, 1 H), 4.00 (s, 3 H), 3.99 (d, J=12.8 Hz, 1 H), 3.89 (d, J=12.8 Hz, 1 H).

Step 2: Trichloroacetic anhydride (0.77 ml, 4.23 mmole, 1 equiv.) was added dropwise over 2 min to a suspension of the product of Step 1 (4.23 mmole, 1 equiv.) in dry CH$_2$Cl$_2$ (40 ml) at 0° C. After 45 min at 0° C., the reaction was quenched with 5% aqueous NaHCO$_3$ (40 ml) and extracted with CH$_2$Cl$_2$. Drying (MgSO$_4$), and concentration gave a yellow solid Silica gel chromatography (3% MeOH/CHCl$_3$) gave 1-methoxy-5H-[1,2]benzisothiazolo[2,3-a]quinoline-5-one (0.81 g, 68%) as a light yellow solid, which was recrystallized from CHCl$_3$ mp phase change at 220–223 ° C., actual mp 225–226 ° C.; TLC (5% MeOH/CHCl$_3$) R$_f$ 0.38; $^1$H NMR (CDCl$_3$) δ8.17 (dd, J=8.1, 1.1 Hz, 1 H), 7.98 (d, J=8.1 Hz, 1 H), 7.53–7.66 (m, 2 H), 7.41–7.50 (m, 1 H), 7.39 (t, J=8.1 Hz, 1 H), 7.18 (app d, 1 H), 7.15 (s, 1 H), 4.13 (s, 3 H); IR (KBr) 1617, 1602, 1580, 1568, 1558, 1452, 1395, 1270, 1041, 799, 762 cm$^{-1}$; MS (NH$_3$), m/e (%) 282.0 (100, (M+H)+). Anal. Calcd for C$_{16}$H$_{11}$NO$_2$S: C, 68.31; H, 3.94; N, 4.98; S, 11.40. Found: C, 68.33; H, 3.81; N, 4.79; S, 11.12.

The compounds of Examples 17–18 were prepared using appropriate reagents and compounds by methods analogous to those used for Example 16.

EXAMPLE 17

1,2,3-Trimethoxy-5H-[1,2]benzisothiazolo2,3-a]quinoline-5-one

Step 1 (sulfoxide): TLC (10% MeOH in 50% EtOAc/CHCl$_3$) R$_f$ 0.44; $^1$H NMR (CDCl$_3$) δ9.57 (br s, 1 H), 7.74 (d, J=7.3 Hz, 1 H), 7.50–7.68 (m, 4 H), 7.22 (d, J=7.7 Hz, 1 H), 7.14 (app t, 2 H), 6.80 (d, J=7.3 Hz, 2 H), 6.27 (d, J=1.9 Hz, 1 H), 4.05 (s, 3 H), 4.011 (s, 3 H), 4.008 (s, 3 H), 3.99 (d, J=13.1 Hz, 1 H), 3.89 (d, J=13.1 Hz, 1 H).

Step 2 (title compound): mp 195.5–196.5° C. (dec; from 2-propanol); TLC (5% MeOH in 50% EtOAc/CHCl$_3$) R$_f$ 0.29; $^1$H NMR (CDCl$_3$) δ8.01 (d, J=8.0 Hz, 1 H), 7.81 (s, 1 H), 7.65 (narrow m, 2 H), 7.45–7.55 (m, 1 H), 7.12 (s, 1 H), 4.17 (s, 3 H), 4.04 (s, 3 H), 4.03 (s, 3 H); IR (KBr) 1599, 1573, 1564, 1549, 1467, 1444, 1424, 1143, 1136, 1104, 1023, 806 cm$^{-1}$; MS (NH$_3$), m/e (%) 342.1 (100, (M+H)+). Anal. Calcd for C$_{18}$H$_{15}$NO$_4$S: C, 63.33; H, 4.43; N, 4.10; S, 9.39. Found: C, 63.27; H, 4.32; N, 4.13; S, 9.14.

EXAMPLE 18

10-Methoxy-5H-[1,2]benzisothiazolo[2,3-a]quinoline-5-one

Step 1 (sulfoxide): TLC (10% MeOH in 50% EtOAc/CHCl$_3$) R$_f$ 0.35; $^1$H NMR (CDCl$_3$) δ11.52 (br s, 1 H), 8.37 (app dd, 1 H), 7.48–7.60 (m, 2 H), 7.30–7.40 (m, 2 H), 7.13–7.30 (m, 4 H), 7.00 (dd, J=8.4, 0.8 Hz, 1 H), 6.92 (app d, 2 H), 6.19 (d, J=1.5 Hz, 1 H), 4.32 (d, J=12.5 Hz, 1 H), 4.26 (d, J=12.5 Hz, 1 H), 3.81 (s, 3 H).

Step 2 (title compound): mp 245–251° C. (from toluene); TLC (3% MeOH/CHCl$_3$) R$_f$ 0.26; $^1$H NMR (CDCl$_3$) δ8.52 (dd, J=7.9, 0.9 Hz, 1 H), 7.68–7.78 (m, 1 H), 7.56 (d, J=7.7 Hz, 1 H), 7.40–7.53 (m, 3 H), 7.00–7.08 (m, 2 H), 4.02 (s, 3 H); IR (KBr) 1623, 1597, 1579, 1551, 1488, 1463, 1277, 1128, 754 cm$^{-1}$; MS (NH$_3$), m/e (%) 282.0 (100, (M+H)+). Anal. Calcd for C$_{16}$H$_{11}$NO$_2$S: C, 68.31; H, 3.94; N, 4.98; S, 11.40. Found: C, 67.99; H, 3.79; N, 4.83; S, 11.20.

EXAMPLE 19

5H-Pyrido[3′,2′:4,5]isothiazolo[2,3]-quinoline-5-one

Step 1: 3-Chloroperoxybenzoic acid (70%, 2.03 g, 8.25 mmole, 1.0 equiv.) was added in three portions at 0.5 min intervals to a suspension of 2-[2-[(phenylmethyl)thio]-3-pyridinyl]-4(1H)-quinolinone (2.84 g, 8.25 mmole, 1.0 equiv.) in CH$_2$Cl$_2$ (165 ml) at 0° C. After 15 min, the solution was washed with 5% aqueous NaHCO$_3$ (3×100 ml). Drying (MgSO$_4$) and concentration gave the crude sulfoxide, which was use without further purification: TLC (10% MeOH in 50% EtOAc/CHCl$_3$) R$_f$ 0.20; $^1$H NMR (CDCl$_3$) δ11.71 (br s, 1 H), 8.61 (app d, 1 H), 8.29 (app d, 1 H), 7 80 (app d, 1 H), 7.24 –7.60 (m, 5 H), 7.18 (app t, 2 H), 6.85 (app d, 2 H), 5.67 (s, 1 H), 4.19 (d, J=13 Hz, 1 H), 4.08 (d, J=13 Hz, 1 H).

Step 2: Trichloroacetic anhydride (1.51 ml, 8.25 mmole, 1 equiv.) was added dropwise over 4 min to a solution of the product of Step 1 (8.25 mmole, 1 equiv.) in dry CH$_2$Cl$_2$ (80 ml) at 0° C. A precipitate separated during the addition. After 1 hr at 0° C., the reaction was filtered and the solid was washed with cold CH$_2$Cl$_2$. The filtrate was discarded. The solid was stirred briskly with CHCl$_3$ (200 ml) and 5% aqueous NaHCO$_3$ (100 ml) for 15 min, then the mixture was filtered. The filter pad was washed thoroughly with H$_2$O and CHCl$_3$, then the solid was dissolved in 10% MeOH/CHCl$_3$. The filtrate was separated, and the aqueous layer was extracted with CHCl$_3$ (1×50 ml). The CHCl$_3$ layers and the MeOH/CHCl$_3$ solution were combined, dried (MgSO$_4$). and filtered through a short pad of silica gel (10% MeOH/CHCl$_3$). Concentration gave 5H-pyrido[3′,2′:4,5]isothiazolo[2,3-a]quinoline-5-one (1.67 g, 80%) as a yellow solid, which was recrystallized from MeOH/CHCl$_3$: mp>350° C.; TLC (10% MeOH in 50% EtOAc/CHCl$_3$) R$_f$ 0.40; $^1$H NMR (CDCl$_3$) δ8.78 (dd, J=4.8, 1.5 Hz, 1 H), 8.54 (dd, J=8.1, 1.5 Hz, 1 H), 8.25 (dd, J=8.1, 1.5 Hz, 1 H), 7.77 (app t, 1 H), 7.45–7.55 (m, 3 H), 7.07 (s, 1 H); IR (KBr) 1615, 1599, 1588, 1575, 1557, 1546, 1480, 1460, 772 cm$^{-1}$; MS (NH$_3$), m/e (%) 253.1 (100, (M+H)+). Anal. Calcd for C$_{14}$H$_8$N$_2$OS: C, 66.65; H, 3.20; N, 11.10; S, 12.71. Found: C, 66.33; H, 3.13; N, 11.04; S, 12.47.

Utility

The compounds of Formula I may be tested for efficacy in a rabbit model of cytokine induced joint inflammation as described by Pettipher et al. Proc.Natl. Acad. Sci. USA (1986) 83: 8749; Dingle et al. Ann. Rheum. Dis. (1987) 46:527 and Arner et al. Agents and Actions (1989) 27:254. For example, the activity of the compounds in blocking IL-1β-induced cellular infiltration into the synovial fluid of rabbits may be assessed, as described below.

Male New Zealand White rabbits (weight 2.5–2.7 kg) were injected intraarticularly into the right rear knee with 5 ng of recombinant human IL-1β (specific activity, 1×10$^7$ units/mg) through the suprapatellar ligament into the joint space in a volume of 0.2 ml phosphate buffered saline (PBS) and sacrificed at 18 hours following treatment; the left knee served as an untreated control. For inhibition studies, test compounds were co-administered with the IL-1β (5 ng IL-1β in 0.2 ml of 100 mM drug prepared in 1% DMSO) and the left knee was injected with drug alone to serve as a paired control (n=5 rabbits per group for each experiment). At 18 hours following challenge, the joint space was washed with 1 ml of PBS and the synovial washes were taken for cell counts. Following Coulter counter analysis of synovial wash for cell counts, samples were centrifuged to remove cells and digested with papain for 2 hours at 65° C. Cartilage proteoglycan breakdown may be assessed by monitoring glycosaminoglycan levels in the synovial fluid wash using the 1,9-dimethylmethylene blue assay (Farndale et al. Conn. Tiss. Res. (1982) 9: 247).

Cytokine stimulated cell influx was determined by comparing the values from the IL-1β-treated knee to the control knee from the same animal. Inhibition was evaluated as follows (1-((D-C)/(IL-C)))×100%; where D is the cell influx concentration in synovial fluid from knees injected with IL-1β plus test compound; IL is the cell influx in synovial fluid from knees injected with IL-1β alone; and C is the cell influx in synovial fluid from paired control knees.

Representative compounds of the invention of Formula I were demonstrated to inhibit joint inflammation in the animal model described above.

The activity of the representative compounds of the invention in vivo, in inhibiting IL-1β-induced joint inflammation indicates that the compounds of the present invention may be clinically useful for the treatment of inflammation and inflammatory diseases, including osteoarthritis and rheumatoid arthritis.

Dosage and Formulation

The compounds of the invention can be administered to treat inflammation, including but not limited to rheumatoid arthritis and osteoarthritis, by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Compositions (dosage forms) suitable for internal administration contain from about 1 milligram to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. It can also be administered by inhalation in the form of a nasal spray or lung inhaler. It can also be administered topically as an ointment, cream, gel, paste, lotion, solution, spray, aerosol, liposome, or patch. Dosage forms used to administer the active ingredient usually contain suitable carriers, diluents, preservatives, or other excipients, as described in Remington's Pharmaceutical Sciences, Mack Publishing Company, a standard reference text in the field.

Gelatin capsules contain the active ingredient and powdered carriers, such as lactose, sucrose, mannitol, starch, cellulose derivatives, magnesium stearate, stearic acid, and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Anti-oxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

The topical ointments, creams, gels, and pastes can contain diluents such as waxes, paraffins, starch, polyethylene glycol, silicones, bentonites, silicic acid, animal and vegetable fats, talc and zinc oxide or mixtures of these or other diluents. Topical solutions and emulsions can, for example, contain the customary diluents (with the exclusion of solvents having a molecular weight below 200 except in the presence of a surface-active agent), such as solvents, dissolving agents and emulsifiers; specific examples are water, ethanol, 2-propanol, ethyl carbonate, benzyl alcohol, propylene glycol, oils, glycerol, and fatty acid esters of sorbitol or mixtures thereof. Compositions for topical dosing may also contain preservatives or anti-oxidizing agents.

Powders and sprays can contain the usual diluents, such as lactose, talc, silicic acid, aluminum hydroxide, calcium silicate, and polyamide powders or mixtures of these materials. Aerosol sprays can contain the usual propellants. Liposomes can be made from such materials as animal or vegetable fats which will form lipid bilayers in which the active ingredient can be incorporated.

Patches can be made of a matrix such as polyacrylamide, and a semipermeable membrane made from a suitable polymer to control the rate at which the material is delivered to the skin.

Examples of useful pharmaceutical compositions for administration of the compounds of this invention can be illustrated as follows:

Capsules: Capsules may be prepared by filling standard two-piece hard gelatin capsules each with 50 mg of powdered active ingredient, 175 mg of lactose, 24 mg of talc, and 6 mg of magnesium stearate.

Soft Gelatin Capsules: A mixture of active ingredient in soybean oil is prepared and injected by means of a positive displacement pump into gelatin to form soft gelatin capsules containing 50 mg of the active ingredient. The capsules are washed in petroleum ether and dried.

Tablets: Tablets may be prepared by conventional procedures so that the dosage unit is 50 mg of active ingredient, 6 mg of magnesium stearate, 70 mg of microcrystalline cellulose, 11 mg of cornstarch, and 225 mg of lactose. Appropriate coatings may be applied to increase palatability or delay absorption.

Suspension: An aqueous suspension is prepared for oral administration so that each 5 ml contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable: A parenteral composition suitable for administration by injection is prepared by stirring 1.5% by weight of active ingredient in 10% by volume propylene glycol and water. The solution is sterilized by commonly used techniques.

Nasal Spray: An aqueous solution is prepared such that each 1 ml contains 10 mg of active ingredient, 1.8 mg methylparaben, 0.2 mg propylparaben and 10 mg methylcellulose. The solution is dispensed into 1 ml vials.

Lung Inhaler: A homogeneous mixture of the active ingredient in polysorbate 80 is prepared such that the final concentration of the active ingredient will be 10 mg per container and the final concentration of polysorbate 80 in the container will be 1% by weight. The mixture is dispensed into each can, the valves are crimped onto the can and the required amount of dichlorotetrafluoroethane is added under pressure.

Ointment: The active ingredient is added to a mixture of 48% by weight white petrolatum, 10% liquid petrolatum, 8% glycerol monostearate, 3% isopropyl myristate, and 20% lanolin at 70° C. After thorough mixing, a warm solution of methyl- and propyl-parabens in water containing sodium acetone bisulfite is added such that the final concentrations of each paraben is 0.15%, of water is 8%, and of sodium acetone bisulfite is 0.5%. The mixture is stirred until it has reached room temperature.

Representative compounds of the invention useful for the treatment of inflammatory diseases, including rheumatoid arthritis and osteoarthritis, are listed below in Table 2. In Table 2, "—" designates that the indicated R group is hydrogen, i.e., that there is no substituent provided by the indicated R group. In Examples Number 128-139, $R^1$ and $R^2$ are taken together to form —$OCH_2O$—.

TABLE 2

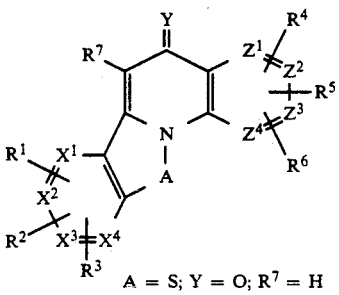

$A = S; Y = O; R^7 = H$

| Ex. No. | $X^1$ | $X^2$ | $X^3$ | $X^4$ | $Z^1$ | $Z^2$ | $Z^3$ | $Z^4$ | $R^1$ | $R^2$ | $R^3$ | $R^4$ | $R^5$ | $R^6$ |
|---|---|---|---|---|---|---|---|---|---|---|---|---|---|---|
| 14 | CH | CH | CH | CH | CH | CH | CH | CH | — | — | — | — | — | — |
| 15 | CH | CH | CH | CH | CH | $CR^4$ | CH | CH | — | — | — | Cl | — | — |
| 16 | CH | CH | CH | CH | CH | CH | CH | $CR^4$ | — | — | — | OMe | — | — |
| 17 | CH | CH | CH | CH | CH | $CR^4$ | $CR^5$ | $CR^6$ | — | — | — | OMe | OMe | OMe |
| 18 | CH | CH | CH | $CR^1$ | CH | CH | CH | CH | OMe | — | — | — | — | — |
| 19 | CH | CH | CH | N | CH | CH | CH | CH | — | — | — | — | — | — |
| 20 | CH | CH | CH | CH | CH | CH | CH | CH | — | — | — | — | — | — |
| 21 | CH | CH | CH | CH | $CR^4$ | CH | CH | CH | — | — | — | Me | — | — |
| 22 | CH | CH | CH | CH | CH | $CR^4$ | CH | CH | — | — | — | Cl | — | — |
| 23 | CH | CH | CH | CH | CH | $CR^4$ | CH | CH | — | — | — | Me | — | — |
| 24 | CH | CH | CH | CH | CH | $CR^4$ | CH | CH | — | — | — | $NO_2$ | — | — |
| 25 | CH | CH | CH | CH | CH | CH | $CR^4$ | CH | — | — | — | Cl | — | — |
| 26 | CH | CH | CH | CH | CH | CH | CH | $CR^4$ | — | — | — | OMe | — | — |
| 27 | CH | CH | CH | CH | CH | CH | CH | $CR^4$ | — | — | — | Me | — | — |
| 28 | CH | CH | CH | CH | CH | $CR^4$ | $CR^5$ | CH | — | — | — | OMe | OMe | — |
| 29 | CH | CH | CH | CH | CH | $CR^4$ | $CR^5$ | $CR^6$ | — | — | — | OMe | OMe | OMe |
| 30 | CH | CH | CH | CH | CH | CH | CH | N | — | — | — | — | — | — |
| 31 | CH | CH | CH | CH | N | CH | CH | N | — | — | — | — | — | — |
| 32 | $CR^1$ | CH | CH | CH | CH | CH | CH | CH | Cl | — | — | — | — | — |
| 33 | $CR^1$ | CH | CH | CH | $CR^4$ | CH | CH | CH | Cl | — | — | Me | — | — |
| 34 | $CR^1$ | CH | CH | CH | CH | $CR^4$ | CH | CH | Cl | — | — | Cl | — | — |
| 35 | $CR^1$ | CH | CH | CH | CH | $CR^4$ | CH | CH | Cl | — | — | Me | — | — |
| 36 | $CR^1$ | CH | CH | CH | CH | $CR^4$ | CH | CH | Cl | — | — | $NO_2$ | — | — |
| 37 | $CR^1$ | CH | CH | CH | CH | CH | $CR^4$ | CH | Cl | — | — | Cl | — | — |
| 38 | $CR^1$ | CH | CH | CH | CH | CH | CH | $CR^4$ | Cl | — | — | OMe | — | — |
| 39 | $CR^1$ | CH | CH | CH | CH | CH | CH | $CR^4$ | Cl | — | — | Me | — | — |
| 40 | $CR^1$ | CH | CH | CH | CH | $CR^4$ | $CR^5$ | CH | Cl | — | — | OMe | OMe | — |
| 41 | $CR^1$ | CH | CH | CH | CH | $CR^4$ | $CR^5$ | $CR^6$ | Cl | — | — | OMe | OMe | OMe |
| 42 | $CR^1$ | CH | CH | CH | CH | CH | CH | N | Cl | — | — | — | — | — |
| 43 | $CR^1$ | CH | CH | CH | N | CH | CH | N | Cl | — | — | — | — | — |
| 44 | CH | $CR^1$ | CH | CH | CH | CH | CH | CH | Me | — | — | — | — | — |
| 45 | CH | $CR^1$ | CH | CH | $CR^4$ | CH | CH | CH | Me | — | — | Me | — | — |
| 46 | CH | $CR^1$ | CH | CH | CH | $CR^4$ | CH | CH | Me | — | — | Cl | — | — |
| 47 | CH | $CR^1$ | CH | CH | CH | $CR^4$ | CH | CH | Me | — | — | Me | — | — |
| 48 | CH | $CR^1$ | CH | CH | CH | $CR^4$ | CH | CH | Me | — | — | $NO_2$ | — | — |
| 49 | CH | $CR^1$ | CH | CH | CH | CH | $CR^4$ | CH | Me | — | — | Cl | — | — |
| 50 | CH | $CR^1$ | CH | CH | CH | CH | CH | $CR^4$ | Me | — | — | OMe | — | — |
| 51 | CH | $CR^1$ | CH | CH | CH | CH | CH | $CR^4$ | Me | — | — | Me | — | — |
| 52 | CH | $CR^1$ | CH | CH | CH | $CR^4$ | $CR^5$ | CH | Me | — | — | OMe | OMe | — |
| 53 | CH | $CR^1$ | CH | CH | CH | $CR^4$ | $CR^5$ | $CR^6$ | Me | — | — | OMe | OMe | OMe |
| 54 | CH | $CR^1$ | CH | CH | CH | CH | CH | N | Me | — | — | — | — | — |
| 55 | CH | $CR^1$ | CH | CH | N | CH | CH | N | Me | — | — | — | — | — |
| 56 | CH | CH | $CR^1$ | CH | CH | CH | CH | CH | Cl | — | — | — | — | — |
| 57 | CH | CH | $CR^1$ | CH | $CR^4$ | CH | CH | CH | Cl | — | — | Me | — | — |
| 58 | CH | CH | $CR^1$ | CH | CH | $CR^4$ | CH | CH | Cl | — | — | Cl | — | — |
| 59 | CH | CH | $CR^1$ | CH | CH | $CR^4$ | CH | CH | Cl | — | — | Me | — | — |
| 60 | CH | CH | $CR^1$ | CH | CH | $CR^4$ | CH | CH | Cl | — | — | $NO_2$ | — | — |

TABLE 2-continued

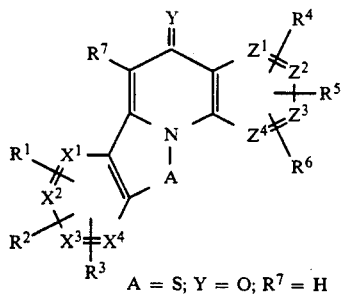

A = S; Y = O; R⁷ = H

| Ex. No. | $X^1$ | $X^2$ | $X^3$ | $X^4$ | $Z^1$ | $Z^2$ | $Z^3$ | $Z^4$ | $R^1$ | $R^2$ | $R^3$ | $R^4$ | $R^5$ | $R^6$ |
|---|---|---|---|---|---|---|---|---|---|---|---|---|---|---|
| 61 | CH | CH | CR¹ | CH | CH | CH | CR⁴ | CH | Cl | — | — | Cl | — | — |
| 62 | CH | CH | CR¹ | CH | CH | CH | CH | CR⁴ | Cl | — | — | OMe | — | — |
| 63 | CH | CH | CR¹ | CH | CH | CH | CH | CR⁴ | Cl | — | — | Me | — | — |
| 64 | CH | CH | CR¹ | CH | CH | CR⁴ | CR⁵ | CH | Cl | — | — | OMe | OMe | — |
| 65 | CH | CH | CR¹ | CH | CH | CR⁴ | CR⁵ | CR⁶ | Cl | — | — | OMe | OMe | OMe |
| 66 | CH | CH | CR¹ | CH | CH | CH | CH | N | Cl | — | — | — | — | — |
| 67 | CH | CH | CR¹ | CH | N | CH | CH | N | Cl | — | — | — | — | — |
| 68 | CH | CH | CR¹ | CH | CH | CH | CH | CH | OMe | — | — | — | — | — |
| 69 | CH | CH | CR¹ | CH | CR⁴ | CH | CH | CH | OMe | — | — | Me | — | — |
| 70 | CH | CH | CR¹ | CH | CH | CR⁴ | CH | CH | Ome | — | — | Cl | — | — |
| 71 | CH | CH | CR¹ | CH | CH | CR⁴ | CH | CH | OMe | — | — | Me | — | — |
| 72 | CH | CH | CR¹ | CH | CH | CR⁴ | CH | CH | OMe | — | — | NO₂ | — | — |
| 73 | CH | CH | CR¹ | CH | CH | CH | CR⁴ | CH | Ome | — | — | Cl | — | — |
| 74 | CH | CH | CR¹ | CH | CH | CH | CH | CR⁴ | OMe | — | — | OMe | — | — |
| 75 | CH | CH | CR¹ | CH | CH | CH | CH | CR⁴ | OMe | — | — | Me | — | — |
| 76 | CH | CH | CR¹ | CH | CH | CR⁴ | CR⁵ | CH | Ome | — | — | OMe | OMe | — |
| 77 | CH | CH | CR¹ | CH | CH | CR⁴ | CR⁵ | CR⁶ | OMe | — | — | OMe | OMe | OMe |
| 78 | CH | CH | CR¹ | CH | CH | CH | CH | N | OMe | — | — | — | — | — |
| 79 | CH | CH | CR¹ | CH | N | CH | CH | N | Ome | — | — | — | — | — |
| 80 | CH | CH | CR¹ | CH | CH | CH | CH | CH | Me | — | — | — | — | — |
| 81 | CH | CH | CR¹ | CH | CR⁴ | CH | CH | CH | Me | — | — | Me | — | — |
| 82 | CH | CH | CR¹ | CH | CH | CR⁴ | CH | CH | Me | — | — | Cl | — | — |
| 83 | CH | CH | CR¹ | CH | CH | CR⁴ | CH | CH | Me | — | — | Me | — | — |
| 84 | CH | CH | CR¹ | CH | CH | CR⁴ | CH | CH | Me | — | — | NO₂ | — | — |
| 85 | CH | CH | CR¹ | CH | CH | CH | CR⁴ | CH | Me | — | — | Cl | — | — |
| 86 | CH | CH | CR¹ | CH | CH | CH | CH | CR⁴ | Me | — | — | OMe | — | — |
| 87 | CH | CH | CR¹ | CH | CH | CH | CH | CR⁴ | Me | — | — | Me | — | — |
| 88 | CH | CH | CR¹ | CH | CH | CR⁴ | CR⁵ | CH | Me | — | — | OMe | OMe | — |
| 89 | CH | CH | CR¹ | CH | CH | CR⁴ | CR⁵ | CR⁶ | Me | — | — | OMe | OMe | OMe |
| 90 | CH | CH | CR¹ | CH | CH | CH | CH | N | Me | — | — | — | — | — |
| 91 | CH | CH | CR¹ | CH | N | CH | CH | N | Me | — | — | — | — | — |
| 92 | CH | CH | CH | CR¹ | CH | CH | CH | CH | Cl | — | — | — | — | — |
| 93 | CH | CH | CH | CR¹ | CR⁴ | CH | CH | CH | Cl | — | — | Me | — | — |
| 94 | CH | CH | CH | CR¹ | CH | CR⁴ | CH | CH | Cl | — | — | Cl | — | — |
| 95 | CH | CH | CH | CR¹ | CH | CR⁴ | CH | CH | Cl | — | — | Me | — | — |
| 96 | CH | CH | CH | CR¹ | CH | CR⁴ | CH | CH | Cl | — | — | NO₂ | — | — |
| 97 | CH | CH | CH | CR¹ | CH | CH | CR⁴ | CH | Cl | — | — | Cl | — | — |
| 98 | CH | CH | CH | CR¹ | CH | CH | CH | CR⁴ | Cl | — | — | OMe | — | — |
| 99 | CH | CH | CH | CR¹ | CH | CH | CH | CR⁴ | Cl | — | — | Me | — | — |
| 100 | CH | CH | CH | CR¹ | CH | CR⁴ | CR⁵ | CH | Cl | — | — | OMe | OMe | — |
| 101 | CH | CH | CH | CR¹ | CH | CR⁴ | CR⁵ | CR⁶ | Cl | — | — | OMe | OMe | OMe |
| 102 | CH | CH | CH | CR¹ | CH | CH | CH | N | Cl | — | — | — | — | — |
| 103 | CH | CH | CH | CR¹ | N | CH | CH | N | Cl | — | — | — | — | — |
| 104 | CH | CH | CH | CR¹ | CH | CH | CH | CH | OMe | — | — | — | — | — |
| 105 | CH | CH | CH | CR¹ | CR⁴ | CH | CH | CH | OMe | — | — | Me | — | — |
| 106 | CH | CH | CH | CR¹ | CH | CR⁴ | CH | CH | OMe | — | — | Cl | — | — |
| 107 | CH | CH | CH | CR¹ | CH | CR⁴ | CH | CH | OMe | — | — | Me | — | — |
| 108 | CH | CH | CH | CR¹ | CH | CR⁴ | CH | CH | OMe | — | — | NO₂ | — | — |
| 109 | CH | CH | CH | CR¹ | CH | CH | CR⁴ | CH | OMe | — | — | Cl | — | — |
| 110 | CH | CH | CH | CR¹ | CH | CH | CH | CR⁴ | OMe | — | — | OMe | — | — |
| 111 | CH | CH | CH | CR¹ | CH | CH | CH | CR⁴ | OMe | — | — | Me | — | — |
| 112 | CH | CH | CH | CR¹ | CH | CR⁴ | CR⁵ | CH | OMe | — | — | OMe | OMe | — |
| 113 | CH | CH | CH | CR¹ | CH | CR⁴ | CR⁵ | CR⁶ | OMe | — | — | OMe | OMe | OMe |
| 114 | CH | CH | CH | CR¹ | CH | CH | CH | N | OMe | — | — | — | — | — |
| 115 | CH | CH | CH | CR¹ | N | CH | CH | N | OMe | — | — | — | — | — |
| 116 | CH | CH | CR¹ | CR² | CH | CH | CH | CH | OMe | OMe | — | — | — | — |
| 117 | CH | CH | CR¹ | CR² | CR⁴ | CH | CH | CH | OMe | OMe | — | Me | — | — |
| 118 | CH | CH | CR¹ | CR² | CH | CR⁴ | CH | CH | OMe | OMe | — | Cl | — | — |
| 119 | CH | CH | CR¹ | CR² | CH | CR⁴ | CH | CH | OMe | OMe | — | Me | — | — |
| 120 | CH | CH | CR¹ | CR² | CH | CR⁴ | CH | CH | OMe | OMe | — | NO₂ | — | — |
| 121 | CH | CH | CR¹ | CR² | CH | CH | CR⁴ | CH | OMe | OMe | — | Cl | — | — |
| 122 | CH | CH | CR¹ | CR² | CH | CH | CH | CR⁴ | OMe | OMe | — | OMe | — | — |
| 123 | CH | CH | CR¹ | CR² | CH | CH | CH | CR⁴ | OMe | OMe | — | Me | — | — |
| 124 | CH | CH | CR¹ | CR² | CH | CR⁴ | CR⁵ | CH | OMe | OMe | — | OMe | OMe | — |
| 125 | CH | CH | CR¹ | CR² | CH | CR⁴ | CR⁵ | CR⁶ | OMe | OMe | — | OMe | OMe | OMe |

TABLE 2-continued

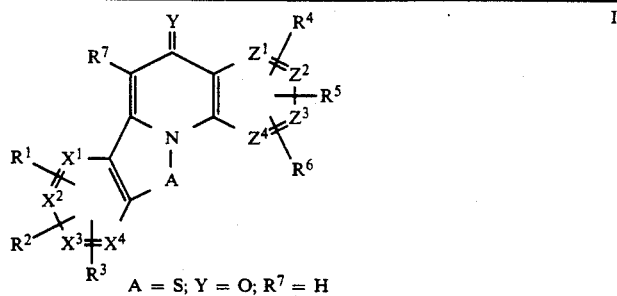

A = S; Y = O; R⁷ = H

| Ex. No. | $X^1$ | $X^2$ | $X^3$ | $X^4$ | $Z^1$ | $Z^2$ | $Z^3$ | $Z^4$ | $R^1$ | $R^2$ | $R^3$ | $R^4$ | $R^5$ | $R^6$ |
|---|---|---|---|---|---|---|---|---|---|---|---|---|---|---|
| 126 | CH | CH | $CR^1$ | $CR^2$ | CH | CH | CH | N | OMe | OMe | — | — | — | — |
| 127 | CH | CH | $CR^1$ | $CR^2$ | N | CH | CH | N | OMe | OMe | — | — | — | — |
| 128 | CH | CH | $CR^1$ | $CR^2$ | CH | CH | CH | CH | —OCH₂O— | | — | — | — | — |
| 129 | CH | CH | $CR^1$ | $CR^2$ | $CR^4$ | CH | CH | CH | —OCH₂O— | | — | Me | — | — |
| 130 | CH | CH | $CR^1$ | $CR^2$ | CH | $CR^4$ | CH | CH | —OCH₂O— | | — | Cl | — | — |
| 131 | CH | CH | $CR^1$ | $CR^2$ | CH | $CR^4$ | CH | CH | —OCH₂O— | | — | Me | — | — |
| 132 | CH | CH | $CR^1$ | $CR^2$ | CH | $CR^4$ | CH | CH | —OCH₂O— | | — | NO₂ | — | — |
| 133 | CH | CH | $CR^1$ | $CR^2$ | CH | CH | $CR^4$ | CH | —OCH₂O— | | — | Cl | — | — |
| 134 | CH | CH | $CR^1$ | $CR^2$ | CH | CH | CH | $CR^4$ | —OCH₂O— | | — | OMe | — | — |
| 135 | CH | CH | $CR^1$ | $CR^2$ | CH | CH | CH | $CR^4$ | —OCH₂O— | | — | Me | — | — |
| 136 | CH | CH | $CR^1$ | $CR^2$ | CH | $CR^4$ | $CR^5$ | CH | —OCH₂O— | | — | OMe | OMe | — |
| 137 | CH | CH | $CR^1$ | $CR^2$ | CH | $CR^4$ | $CR^5$ | $CR^6$ | —OCH₂O— | | — | OMe | OMe | OMe |
| 138 | CH | CH | $CR^1$ | $CR^2$ | CH | CH | CH | N | —OCH₂O— | | — | — | — | — |
| 139 | CH | CH | $CR^1$ | $CR^2$ | N | CH | CH | N | —OCH₂O— | | — | — | — | — |
| 140 | CH | $CR^1$ | $CR^2$ | $CR^3$ | CH | CH | CH | CH | OMe | OMe | OMe | — | — | — |
| 141 | CH | $CR^1$ | $CR^2$ | $CR^3$ | $CR^4$ | CH | CH | CH | OMe | OMe | OMe | Me | — | — |
| 142 | CH | $CR^1$ | $CR^2$ | $CR^3$ | CH | $CR^4$ | CH | CH | OMe | OMe | OMe | Cl | — | — |
| 143 | CH | $CR^1$ | $CR^2$ | $CR^3$ | CH | $CR^4$ | CH | CH | OMe | OMe | OMe | Me | — | — |
| 144 | CH | $CR^1$ | $CR^2$ | $CR^3$ | CH | $CR^4$ | CH | CH | OMe | OMe | OMe | NO₂ | — | — |
| 145 | CH | $CR^1$ | $CR^2$ | $CR^3$ | CH | CH | $CR^4$ | CH | OMe | OMe | OMe | Cl | — | — |
| 146 | CH | $CR^1$ | $CR^2$ | $CR^3$ | CH | CH | CH | $CR^4$ | OMe | OMe | OMe | OMe | — | — |
| 147 | CH | $CR^1$ | $CR^2$ | $CR^3$ | CH | CH | CH | $CR^4$ | OMe | OMe | OMe | Me | — | — |
| 148 | CH | $CR^1$ | $CR^2$ | $CR^3$ | CH | $CR^4$ | $CR^5$ | CH | OMe | OMe | OMe | OMe | OMe | — |
| 149 | CH | $CR^1$ | $CR^2$ | $CR^3$ | CH | $CR^4$ | $CR^5$ | $CR^6$ | OMe | OMe | OMe | OMe | OMe | OMe |
| 150 | CH | $CR^1$ | $CR^2$ | $CR^3$ | CH | CH | CH | N | OMe | OMe | OMe | — | — | — |
| 151 | CH | $CR^1$ | $CR^2$ | $CR^3$ | N | CH | CH | N | OMe | OMe | OMe | — | — | — |
| 152 | CH | CH | CH | N | CH | CH | CH | CH | Me | — | — | — | — | — |
| 153 | CH | CH | CH | N | $CR^4$ | CH | CH | CH | Me | — | — | Me | — | — |
| 154 | CH | CH | CH | N | CH | $CR^4$ | CH | CH | Me | — | — | Cl | — | — |
| 155 | CH | CH | CH | N | CH | $CR^4$ | CH | CH | Me | — | — | Me | — | — |
| 156 | CH | CH | CH | N | CH | $CR^4$ | CH | CH | Me | — | — | NO₂ | — | — |
| 157 | CH | CH | CH | N | CH | CH | $CR^4$ | CH | Me | — | — | Cl | — | — |
| 158 | CH | CH | CH | N | CH | CH | CH | $CR^4$ | Me | — | — | OMe | — | — |
| 159 | CH | CH | CH | N | CH | CH | CH | $CR^4$ | Me | — | — | Me | — | — |
| 160 | CH | CH | CH | N | CH | $CR^4$ | $CR^5$ | CH | Me | — | — | OMe | OMe | — |
| 161 | CH | CH | CH | N | CH | $CR^4$ | $CR^5$ | $CR^6$ | Me | — | — | OMe | OMe | OMe |
| 162 | CH | CH | CH | N | CH | CH | CH | N | Me | — | — | — | — | — |
| 163 | CH | CH | CH | N | N | CH | CH | N | Me | — | — | — | — | — |

What is claimed is:

1. A compound of Formula I:

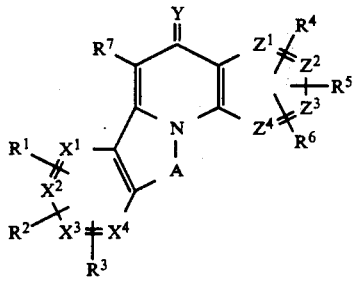

or a pharmaceutically acceptable salt or prodrug form thereof, wherein:

$X^1$, $X^2$, $X^3$, and $X^4$ are CH;
$Z^1$, $Z^2$, $Z^3$, and $Z^4$ are CH;
Y is O or S;
A is S or Se;
$R^1$, $R^2$, $R^3$, $R^4$, $R^5$, and $R^6$ are independently selected from the following groups:
hydrogen;
$C_1$–$C_8$ alkyl substituted with 0–3 $R^{20}$;
$C_2$–$C_8$ alkenyl substituted with 0–3 $R^{20}$;
$C_2$–$C_8$ alkynyl substituted with 0–3 $R^{20}$;
$C_3$–$C_8$ cycloalkyl substituted with 0–3 $R^{20}$;
$C_6$–$C_{10}$ bicycloalkyl substituted with 0–3 $R^{20}$;
phenyl substituted with 0–3$R^{21}$; naphthyl substituted with 0–3$R^{21}$;
F; Cl; Br; I; NO₂;
$OR^{12}$; $OC(=O)R^{12}$; $OC(=O)OR^{12}$; $OC(=O)ON(R^{12})_2$;
$N(R^{12})_2$; $NR^{12}C(=O)R^{12}C(=O)OR^{12}$; $NR^{12}SO_2R^{12}$; $NR^{12}C(=O)N(R^{12})_2$;
$SO_3H$; $SR^{12}$; $S(O)R^{12}$; $SO_2R^{12}$; $SO_2N(R^{12})_2$;
$C(=O)R^{12}$; $CO_2R^{12}$; $C(=O)N(R^{12})_2$; $CSN(R^{12})_2$; $C(=O)NR^{12}OR^{12}$; and CN;

$R^1$ and $R^2$, when an adjacent carbon atoms, may alternatively be taken together to form —OCH$_2$O— or —OCH$_2$CH$_2$O—;

$R^7$ is selected from the group consisting of:
hydrogen;
C$_1$-C$_8$ alkyl substituted with 0-3 $R^{20}$;
C$_2$-C$_8$ alkyenyl substituted with 0-3 $R^{20}$;
C$_2$-C$_8$ alkynyl substituted with 0-3 $R^{20}$;
C$_3$-C$_8$ cycloalkyl substituted with 0-3 $R^{20}$;
C$_6$-C$_{10}$ bicycloalkyl substituted with 0-3 $R^{20}$;
phenyl substituted with 0-3$R^{21}$; naphthyl substituted with 0-3$R^{21}$;
F; Cl; Br; I; NO$_2$;
OR$^{12}$; OC(=O)R$^{12}$; OC(=O)OR$^{12}$; OC(=O)ON(R$^{12}$)$_2$;
N(R$^{12}$)$_2$; NR$^{12}$C(=O)R$^{12}$; NR$^{12}$C(=O)OR$^{12}$; NR$^{12}$SO$_2$R$^{12}$; NR$^{12}$C(=O)N(R$^{12}$)$_2$;
SO$_3$H; SR$^{12}$; S(O)R$^{12}$; SO$_2$R$^{12}$; SO$_2$N(R$^{12}$)$_2$;
C(=O)R$^{12}$; CO$_2$R$^{12}$; C(=O)N(R$^{12}$)$_2$; CSN(R$^{12}$)$_2$;
C(=O)NR$^{12}$OR$^{12}$; and CN;

$R^{12}$ is independently selected at each occurrence from the group consisting of:
hydrogen;
C$_1$-C$_8$ alkyl substituted with 0-3 $R^{20}$;
C$_2$-C$_8$ alkenyl substituted with 0-3 $R^{20}$;
C$_2$-C$_8$ alkynyl substituted with 0-3 $R^{20}$;
C$_3$-C$_8$ cycloalkyl substituted with 0-3 $R^{20}$;
C$_6$-C$_{10}$ bicycloalkyl substituted with 0-3 $R^{20}$;
phenyl substituted with 0-3$R^{21}$; naphthyl substituted with 0-3$R^{21}$;

$R^{20}$ is independently selected at each occurence from the group consisting of:
C$_1$-C$_5$ alkyl; C$_2$-C$_4$ alkenyl; C$_3$-C$_{10}$ cycloalkyl; C$_3$-C$_6$ cycloalkylmethyl; C$_2$-C$_6$ alkoxyalkyl;
—C(=O)NR$^{23}$R$^{24}$; —C(=O)NR$^{23}$OR$^{23}$; CN;
—C(=NH)NHR$^{23}$; —CO$_2$R$^{23}$; —C(=O)R$^{23}$;
—CSN(R$^{23}$)$_2$;
—OC(=O)R$^{23}$; —OC(=O)OR$^{23}$; —OR$^{23}$; —OC(=O)NR$^{23}$R$^{24}$; —NR$^{23}$R$^{24}$;
—NHC(=NH)NHR$^{23}$; —NR$^{24}$C(=O)R$^{23}$; =NOR$^{24}$; —NR$^{24}$C(=O)OR$^{24}$; —NR$^{23}$C(=O)NR$^{23}$R$^{24}$; —NR$^{24}$SO$_2$NR$^{23}$R$^{24}$; —NR$^{24}$SO$_2$R$^{23}$;
SO$_3$H; SR$^{23}$; —S(=O)R$^{23}$; —SO$_2$R$^{23}$; —SO$_2$NR$^{23}$R$^{24}$; keto; F; Cl; Br; I; NO$_2$;
phenyl substituted with 0-3$R^{21}$; naphthyl substituted with 0-3$R^{21}$;

$R^{21}$, when a substituent on carbon, is independently selected at each occurrence from the group consisting of:
phenyl, benzyl, phenethyl, phenoxy, benzyloxy, halogen, hydroxy, nitro, cyano, C$_1$-C$_5$ alkyl, C$_3$-C$_{10}$ cycloalkyl, C$_3$-C$_6$ cycloalkylmethyl, C$_7$-C$_{10}$ alkyl phenyl, C$_7$-C$_{10}$ alkyl naphthyl, C$_1$-C$_4$ alkoxy, —NR$^{23}$R$^{24}$, C$_2$-C$_6$ alkoxyalkyl, C$_1$-C$_4$ hydroxyalkyl, methylenedioxy, ethylenedioxy, C$_1$-C$_4$ haloalkyl, C$_1$-C$_4$ haloalkoxy, C$_1$-C$_4$ alkoxycarbonyl, C$_1$-C$_4$ alkylcarbonyloxy, C$_1$-C$_4$ alkylcarbonyl, C$_1$-C$_4$ alkylcarbonylamino, —SO$_2$R$^{23}$, —S(=O)R$^{23}$, —SO$_2$NR$^{23}$R$^{24}$, SO$_3$H, CF$_3$, OR$^{23}$, CHO, CH$_2$OR$^{23}$, CO$_2$R$^{23}$, C(=O)R$^{23}$, —NHSO$_2$R$^{24}$, —OCH$_2$CO$_2$H;

or $R^{21}$ may be a 3- or 4- carbon chain attached to adjacent carbons on the ring to form a fused 5- or 6-membered ring, said 5- or 6-membered ring being optionally substituted on the aliphatic carbons with halogen, C$_1$-C$_4$ alkyl, C$_1$-C$_4$ alkoxy, hydroxy, or —NR$^{23}$R$^{24}$; or, when $R^{21}$ is attached to a saturated carbon atom, it may be carbonyl or thiocarbonyl;

$R^{23}$ is H, phenyl, benzyl or C$_1$-C$_6$ alkyl;
$R^{24}$ is H, phenyl, benzyl or C$_1$-C$_6$ alkyl;
$R^{23}$ and $R^{24}$ can alternatively join to form —(CH$_2$)$_4$—, —(CH$_2$)$_5$—, —CH$_2$CH$_2$N(R$^{25}$)CH$_2$CH$_2$—, or —CH$_2$CH$_2$OCH$_2$CH$_2$—;
$R^{25}$ is H or CH$_3$;

2. A compound of claim 1, wherein:
$X^1$, $X^2$, $X^3$, and $X^4$ are CH;
$Z^1$, $Z^2$, $Z^3$, and $Z^4$ are CH;
Y is oxygen;
A is sulfur;
$R^1$, $R^2$, $R^3$, $R^4$, $R^5$, and $R^6$ are independently selected from the following groups:
hydrogen;
C$_1$-C$_8$ alkyl substituted with 0-1 $R^{20}$;
C$_2$-C$_8$ alkenyl substituted with 0-1 $R^{20}$;
C$_2$-C$_8$ alkynyl substituted with 0-1 $R^{20}$;
C$_3$-C$_8$ cycloalkyl substituted with 0-1 $R^{20}$;
C$_6$-C$_{10}$ bicycloalkyl substituted with 0-1 $R^{20}$;
phenyl substituted with 0-3$R^{21}$; naphthyl substituted with 0-3$R^{21}$;
F; Cl; Br; I; NO$_2$;
OR$^{12}$;
N(R$^{12}$)$_2$; NR$^{12}$C(=O)R$^{12}$; NR$^{12}$C(=O)OR$^{12}$; NR$^{12}$SO$_2$R$^{12}$; NR$^{12}$C(50 O)N(R$^{12}$)$_2$;
S(O)R$^{12}$; SO$_2$R$^{12}$; SO$_2$N(R$^{12}$)$_2$;
C(=O)R$^{12}$; CO$_2$R$^{12}$; C(=O)N(R$^{12}$)$_2$; C(=O)N(R$^{12}$)$_2$; C(=O)NR$^{12}$OR$^{12}$; and CN;

$R^1$ and $R^2$, when on adjacent carbon atoms, may alternatively be taken together to form —OCH$_2$O—or —OCH$_2$CH$_2$O—;

$R^7$ is selected from the group consisting of:
hydrogen;
C$_1$-C$_8$ alkyl substituted with 0-1 $R^{20}$;
C$_2$-C$_8$ alkenyl substituted with 0-1 $R^{20}$;
C$_2$-C$_8$ alkynyl substituted with 0-1 $R^{20}$;
C$_3$-C$_8$ cycloalkyl substituted with 0-1 $R^{20}$;
C$_6$-C$_{10}$ bicycloalkyl substituted with 0-1 $R^{20}$;
phenyl substituted with 0-3$R^{21}$; naphthyl substituted with 0-3$R^{21}$;
F; Cl; Br; I; NO$_2$;
OR$^{12}$;
N(R$^{12}$)$_2$; NR$^{12}$C(=O)R$^{12}$; NR$^{12}$; NR$^{12}$SO$_2$R$^{12}$; NR$^{12}$C(=O)N(R$^{12}$)$_2$;
S(O)R$^{12}$; SO$_2$R$^{12}$; SO$_2$N(R$^{12}$)$_2$;
C(=O)R$^{12}$; CO$_2$R$^{12}$; C(=O)N(R$^{12}$)$_2$; C(=O)NR$^{12}$OR$^{12}$; and CN;

$R^{12}$ is independently selected at each occurence from the groups consisting of:
hydrogen;
C$_1$-C$_8$ alkyl;
C$_2$-C$_8$ alkenyl;
C$_2$-C$_8$ alkynyl;
C$_3$-C$_8$ cycloalkyl;
C$_6$-C$_{10}$ bicycloalkyl;
phenyl substituted with 0-3 $R^{21}$;

$R^{20}$ is independently selected at each occurence from the group consisting of:
C$_1$-C$_5$ alkyl; C$_2$-C$_4$ alkenyl; C$_3$-C$_{10}$ cycloalkyl; C$_3$-C$_6$ cycloalkylmethyl; C$_2$-C$_6$ alkoxyalkyl;
—C(=O)NR$^{23}$R$^{24}$; —C(=O)NR$^{23}$OR$^{23}$; CN;
—C(=NH)NHR$^{23}$; —CO$_2$R$^{23}$; —C(=O)R$^{23}$;
—CSN(R$^{23}$)$_2$;
—OC(=O)R$^{23}$; —OC(=O)OR$^{23}$; —OR$^{23}$; —OC(=O)NR$^{23}$R$^{24}$; —NR$^{23}$R$^{24}$;

—NHC(=NH)NHR$^{23}$; —NR$^{24}$C(=O)R$^{23}$; =NOR$^{24}$; —NR$^{24}$C(=O)OR$^{24}$; —NR$^{23}$C(=O)NR$^{23}$R$^{24}$; —NR$^{24}$SO$_2$NR$^{23}$R$^{24}$; —NR$^{24}$SO$_2$R$^{23}$;

keto; F; Cl; Br; I; NO$_2$;

phenyl substituted with 0–1R$^{21}$; naphthyl substituted with 0–1R$^{21}$;

R$^{21}$, when a substituent on carbon, is independently selected at each occurrence from the group consisting of:

phenyl, benzyl, phenethyl, phenoxy, benzyloxy, halogen, hydroxy, nitro, cyano, C$_1$–C$_5$ alkyl, C$_3$–C$_{10}$ cycloalkyl, C$_3$–C$_6$ cycloalkylmethyl, C$_7$–C$_{10}$ alkylphenyl, C$_7$–C$_{10}$ alkyl naphthyl, C$_1$–C$_4$ alkoxy, —NR$^{23}$R$^{24}$, C$_2$–C$_6$ alkoxyalkyl, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino; CF$_3$; OR$^{23}$; CHO; CH$_2$OR$^{23}$; CO$_2$R$^{23}$; C(=O)R$^{23}$; or R$^{23}$ is H, phenyl, benzyl or C$_1$–C$_6$ alkyl;

R$^{24}$ is H, phenyl, benzyl or C$_1$–C$_6$ alkyl;

3. A compound of claim 1, wherein:
X$^1$, X$^2$, X$^3$, and X$^4$ are CH;
Z$^1$, Z$^2$, Z$^3$, and Z$^4$ are CH;
A is sulfur;
Y is oxygen;
R$^1$, R$^2$, R$^3$, R$^4$, R$^5$, and R$^6$ are independently selected from the following groups;
hydrogen;
C$_1$–C$_8$ alkyl substituted with 0–1 R$^{20}$;
C$_2$–C$_8$ alkenyl;
C$_2$–C$_8$ alkynyl;
C$_3$–C$_8$ cycloalkyl;
C$_6$–C$_{10}$ bicycloalkyl;
phenyl substituted with 0–1 R$^{21}$;
F; Cl; Br; I; NO$_2$;
OR$^{12}$;
N(R$^{12}$)$_2$; NR$^{12}$C(=O)R$^{12}$; NR$^{12}$C(=O)OR$^{12}$; NR$^{12}$SO$_2$R$^{12}$; NR$^{12}$C(=O)N(R$^{12}$)$_2$;
S(O)R$^{12}$; SO$_2$R$^{12}$; SO$_2$N(R$^{12}$)$_2$;
C(=O)R$^{12}$; CO$_2$R$^{12}$; C(=O)N(R$^{12}$)$_2$; C(=O)NR$^{12}$OR$^{12}$; and CN;

R$^1$ and R$^2$, when an adjacent carbon atoms, may alternatively be taken together to form —OCH$_2$O— or —OCH$_2$CH$_2$O—;

R$^7$ is selected from the following groups:
hydrogen;
C$_1$–C$_8$ alkyl substituted with 0–1 R$^{20}$;
C$_2$–C$_8$ alkenyl;
C$_2$–C$_8$ alkynyl;
C$_3$–C$_8$ cycloalkyl;
C$_6$–C$_{10}$ bicycloalkyl;
phenyl substituted with 0–1 R$^{21}$;
F; Cl; Br; I; NO$_2$;
OR$^{12}$;
N(R$^{12}$)$_2$; NR$^{12}$C(=O)R$^{12}$; NR$^{12}$C(=O)OR$^{12}$; NR$^{12}$SO$_2$R$^{12}$; NR$^{12}$C(=O)N(R$^{12}$)$_2$;
S(O)R$^{12}$; SO$_2$R$^{12}$; SO$_2$N(R$^{12}$)$_2$;
C(=O)R$^{12}$; CO$_2$R$^{12}$; C(=O)N(R$^{12}$)$_2$; C(=O)NR$^{12}$OR$^{12}$; and CN;

R$^{12}$ is independently selected at each occurence from the group consisting of:
hydrogen;
C$_1$–C$_8$ alkyl;
C$_2$–C$_8$ alkenyl;
C$_2$–C$_8$ alkynyl;
C$_3$–C$_8$ cycloalkyl;
C$_6$–C$_{10}$ bicycloalkyl;
phenyl substituted with 0–3 R$^{21}$;

R$^{20}$ is independently selected at each occurence from the group consisting of:

C$_1$–C$_5$ alkyl; C$_2$–C$_4$ alkenyl; C$_3$–C$_{10}$ cycloalkyl; C$_3$–C$_6$ cycloalkylmethyl; C$_2$–C$_6$ alkoxyalkyl; —C(=O)NR$^{23}$R$^{24}$; —C(=O)NR$^{23}$OR$^{23}$; CN; —C(=NH)NHR$^{23}$; —CO$_2$R$^{23}$; —C(=O)R$^{23}$; —CSN(R$^{23}$)$_2$;

—OC(=O)R$^{23}$; —OC(=O)OR$^{23}$; —OR$^{23}$; —OC(=O)NR$^{23}$R$^{24}$; —NR$^{23}$R$^{24}$; —NHC(=NH)NHR$^{23}$; —NR$^{24}$C(=O)R$^{23}$; =NOR$^{24}$; —NR$^{24}$C(=O)OR$^{24}$; —NR$^{23}$C(=O)NR$^{23}$R$^{24}$; —NR$^{24}$SO$_2$NR$^{23}$R$^{24}$; —NR$^{24}$SO$_2$R$^{23}$;

keto; F; Cl; Br; I; NO$_2$;

phenyl substituted with 0–1R$^{21}$; naphthyl substituted with 0–1R$^{21}$;

R$^{21}$, when a substituent on carbon, is independently selected at each occurence from the group consisting of:

phenyl, benzyl, phenethyl, phenoxy, benzyloxy, halogen, hydroxy, nitro, cyano, C$_1$–C$_5$ alkyl, C$_3$–C$_{10}$ cycloalkyl, —NR$^{23}$R$^{24}$, CF$_3$, OR$^{23}$, CHO, CH$_2$OR$^{23}$, CO$_2$R$^{23}$, C(=O)R$^{23}$, R$^{23}$ is H, phenyl, benzyl or C$_1$–C$_6$ alkyl;

R$^{24}$ is H or C$_1$–C$_4$ alkyl.

4. A compound of claim 1, wherein:
X$^1$, X$^2$, X$^3$, and X$^4$ are CH;
Z$^1$, Z$^2$, Z$^3$, and Z$^4$ are CH;
A is sulfur;
Y is oxygen;
R$^1$, R$^2$, R$^3$, R$^4$, R$^5$, and R$^6$ are independently selected from the group consisting of: hydrogen, OCH$_3$, halogen, CH$_3$ or NO$_2$; and
R$^7$ is H.

5. A compound of claim 4, or a pharmaceutically acceptable salt or prodrug thereof, selected from the group consisting of:

5H-[1,2]benzisothiazolo[2,3-a]quinoline-5-one;

3-chloro-5H-[1,2]benzisothiazolo[2,3-a]quinoline-5-one;

1-methoxy-5H-[1,2]benzisothiazolo[2,3-a]quinoline-5-one;

1,2,3-trimethoxy-5H-[1,2]benzisothiazolo[2,3a]quinoline-5-one;

10-methoxy-5H-[1,2]benzisothiazolo[2,3-a]quinoline-5-one; and

6. A pharmaceutical composition comprising a therapeutically effective amount of a compound of claim 1 and a pharmaceutically acceptable carrier.

7. A pharmaceutical composition comprising a therapeutically effective amount of a compound of claim 2 and a pharmaceutically acceptable carrier.

8. A pharmaceutical composition comprising a therapeutically effective amount of a compound of claim 3 and a pharmaceutically acceptable carrier.

9. A pharmaceutical composition comprising a therapeutically effective amount of a compound of claim 4 and a pharmaceutically acceptable carrier.

10. A pharmaceutical composition comprising a therapeutically effective amount of a compound of claim 5 and a pharmaceutically acceptable carrier.

11. A method of treating an inflammatory disease comprising administering to a mammal in need of such treatment a therapeutically effective anti-inflammatory amount of a compound of claim 1.

12. A method of treating an inflammatory disease comprising administering to a mammal in need of such treatment a therapeutically effective anti-inflammatory amount of a compound of claim 2.

13. A method of treating an inflammatory disease comprising administering to a mammal in need of such treatment a therapeutically effective anti-inflammatory amount of a compound of claim 3.

14. A method of treating an inflammatory disease comprising administering to a mammal in need of such treatment a therapeutically effective anti-inflammatory amount of a compound of claim 4.

15. A method of treating an inflammatory disease comprising administering to a mammal in need of such treatment a therapeutically effective anti-inflammatory amount of a compound of claim 5.

16. A method of claim 11 wherein the inflammatory disease is rheumatoid arthritis or osteoarthritis.

* * * * *